(12) United States Patent
Sunjic et al.

(10) Patent No.: US 6,437,167 B1
(45) Date of Patent: Aug. 20, 2002

(54) CHIRAL STATIONARY PHASES FOR ENANTIOMERS SEPARATION AND THEIR PREPARATION

(75) Inventors: Vitomir Sunjic; Darko Kontrec; Vladimir Vinkovic, all of Zagreb (HR)

(73) Assignee: Societa' Cooperative Centro Ricerche Polytech A Responsabilitia' Limitata, Trieste (IT)

( * ) Notice: Subject to any disclaimer, the term of this patent is extended or adjusted under 35 U.S.C. 154(b) by 0 days.

(21) Appl. No.: 09/719,194

(22) PCT Filed: Apr. 28, 1999

(86) PCT No.: PCT/EP99/02869

§ 371 (c)(1),
(2), (4) Date: Dec. 8, 2000

(87) PCT Pub. No.: WO00/00464

PCT Pub. Date: Jan. 6, 2000

(30) Foreign Application Priority Data

Jun. 30, 1998 (IT) .......................................... MI98A1502

(51) Int. Cl.[7] .......................... C07C 255/51; C07F 7/04
(52) U.S. Cl. ...................... 558/419; 558/414; 556/465; 556/466
(58) Field of Search ................................. 558/419, 414; 556/466, 465

(56) References Cited

FOREIGN PATENT DOCUMENTS

| WO | 9306080 | 4/1993 |
|---|---|---|
| WO | 9400408 | 1/1994 |
| WO | 9639377 | 12/1996 |

OTHER PUBLICATIONS

Journal of Chromatography, 186 (1979) 543–552 Elsevier Scientific Publishing Company, Amsterdam—Printed in the Netherlands.

J. Am. Chem. Soc. 1986,108,352–354.

*Primary Examiner*—Floyd D. Higel
*Assistant Examiner*—Ebenezer Sackey
(74) *Attorney, Agent, or Firm*—Hedman & Costigan, P.C.

(57) ABSTRACT

The present invention describes new chiral stationary phases and optically active compounds therein contained. The optically active compounds contained in the stationary phases are represented by the formula of structure (I), containing at least one asymmetric carbon atom, and a substituent acting as a spacer. The stationary phases of the present invention are useful in the preparation of chromatographic columns useful for the separation of enantiomers.

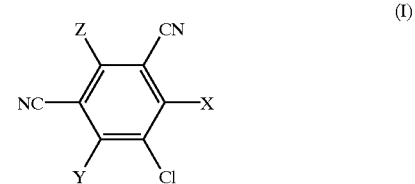

(I)

12 Claims, 21 Drawing Sheets

Figure 5a

Figure 1:
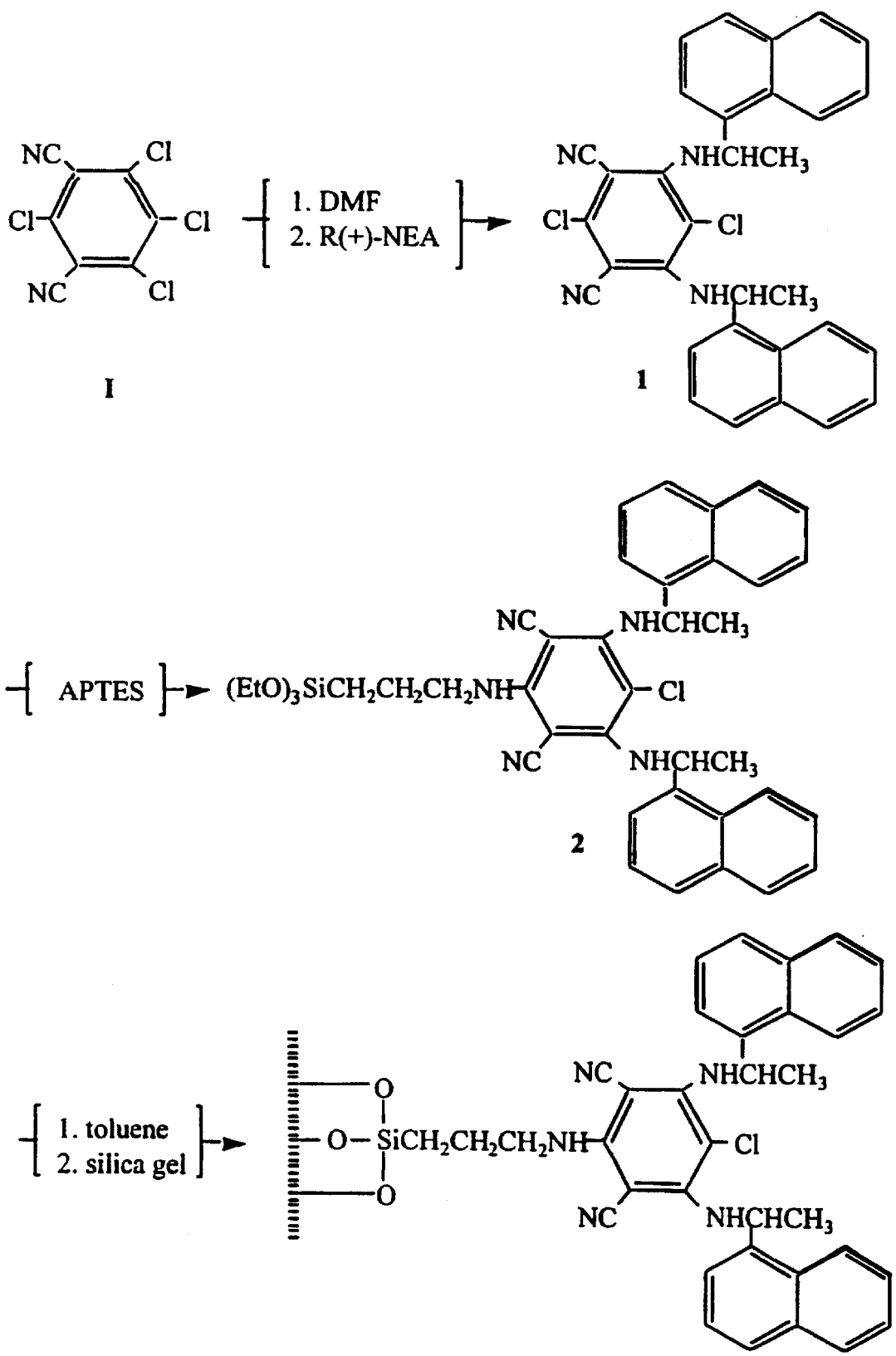

| Sample | Z | X | Y |
|---|---|---|---|
| FSC 1 | —NH(CH₂)₃Si(O–)₃ solid support | —NH—CHCH₃—(naphthyl) | —NH—CHCH₃—(naphthyl) |
| FSC 2 | —Cl | —NH—CH(CH₂-phenyl)—CO—NH(CH₂)₃Si(O–)₃ solid support | —Cl |
| FSC 3 | —NH(CH₂)₃Si(O–)₃ solid support | —NH—CH(CH₂-phenyl)—CONH—(3,5-dimethylphenyl) | —Cl |

Figure 5b

| Sample | Z | X | Y |
|---|---|---|---|
| *FSC 3* | —Cl | ![X structure with dimethylphenyl](NH—CH—CONH— with CH2-phenyl and 3,5-dimethylphenyl) | —NH(CH2)3Si(O—)3—solid support |
| *FSC 4* | —Cl | —NH—CH(CH2-phenyl)—CONH—naphthyl | —NH(CH2)3Si(O—)3—solid support |
| *FSC 4* | —NH(CH2)3Si(O—)3—solid support | —NH—CH(CH2-phenyl)—CONH—naphthyl | —Cl |

Figure 5c

| Sample | Z | X | Y |
|---|---|---|---|
| FSC 5 | —Cl | —NH—CH(phenyl)—CO—NH(CH₂)₃Si(O)(O)(O)—solid support | —Cl |
| FSC 6 | —Cl | —NH—CHCH₃(naphthyl) | —NH(CH₂)₃Si(O)(O)(O)—solid support |
| FSC 6 | —NH(CH₂)₃Si(O)(O)(O)—solid support | —NH—CHCH₃(naphthyl) | —Cl |

Figure 5d

| Sample | Z | X | Y |
|---|---|---|---|
| FSC 7 | —Cl | —N(—CH₂CONH—CHCH₃-naphthyl)(—(CH₂)₃CH₃) | —NH(CH₂)₃Si(O—)₃ solid support |
| FSC 7 | —NH(CH₂)₃Si(O—)₃ solid support | —N(—CH₂CONH—CHCH₃-naphthyl)(—(CH₂)₃CH₃) | —Cl |
| FSC 8 | —Cl | —N(—CH₂CON(—CH(cyclohexyl)CH₃)(—CH₂-naphthyl))(—(CH₂)₃CH₃) | —NH(CH₂)₃Si(O—)₃ solid support |

| Sample | Z | X | Y |
|---|---|---|---|
| FSC 8 |  |  | —Cl |
| FSC 9 |  |  | —Cl |

| Sample | Z | X | Y |
|---|---|---|---|
| FSC 9 | —Cl |  |  |
| FSC 10 | —Cl |  |  |

Figure 5g

| Sample | Z | X | Y |
|---|---|---|---|
| FSC 10 | —NH(CH₂)₃Si(—O—)(—O—)(—O—) solid support | —NHCH₂CH₂NHCOCHCH₃ — (naphthalene) —OCH₃ | |
| FSC 11 | —Cl | —N(—CH₃)—CH₂—CONH—CH(—CH₃)— (naphthalene) | —NH(CH₂)₃Si(—O—)(—O—)(—O—) solid support |
| FSC 11 | —NH(CH₂)₃Si(—O—)(—O—)(—O—) solid support | —N(—CH₃)—CH₂—CONH—CH(—CH₃)— (naphthalene) | —Cl |

Figure 5h

| Sample | Z | X | Y |
|---|---|---|---|
| FSC 12 | —Cl | —NH—CH(CH₃)—CONH(CH₂)₃Si(O—)(O—)(O—) solid support | —Cl |
| FSC 13 | —Cl | —NH—CH(CH₂CONH₂)—CONH(CH₂)₃Si(O—)(O—)(O—) solid support | —Cl |
| FSC 14 | —Cl | —NH—CH(CH₃)—CONH—(3,5-dimethylphenyl) | —NH(CH₂)₃Si(O—)(O—)(O—) solid support |

Figure 5i

| Sample | Z | X | Y |
|---|---|---|---|
| FSC 14 | —NH(CH₂)₃Si(O)₃—solid support | —NH—CH(CH₃)—CONH—(3,5-dimethylphenyl) | —Cl |
| FSC 15 | —Cl | —NH—CH(CH₃)—CONH—cyclohexyl | —NH(CH₂)₃Si(O)₃—solid support |
| FSC 15 | —NH(CH₂)₃Si(O)₃—solid support | —NH—CH(CH₃)—CONH—cyclohexyl | —Cl |

Figure 5j

| Sample | Z | X | Y |
|---|---|---|---|
| FSC 16 | —Cl | 3,5-dimethylphenyl-CONH-pyrrolidine (N-methyl) | —NH(CH₂)₃Si(O–)(O–)(O–)—solid support |
| FSC 16 | —NH(CH₂)₃Si(O–)(O–)(O–)—solid support | 3,5-dimethylphenyl-CONH-pyrrolidine (N-methyl) | —Cl |
| FSC 17 | —Cl | cyclohexyl-CONH-pyrrolidine (N-methyl) | —NH(CH₂)₃Si(O–)(O–)(O–)—solid support |

Figure 5k

| Sample | Z | X | Y |
|---|---|---|---|
| FSC 17 | —NH(CH₂)₃Si(O-)(O-)(O—solid support) | cyclohexyl-CONH-pyrrolidine (N-CH₃) | —Cl |
| FSC 18 | —Cl | CH(CH₃)-CONH-(3,5-dimethylphenyl), CONH-pyrrolidine(N-CH₃) | —NH(CH₂)₃Si(O-)(O-)(O—solid support) |
| FSC 18 | —NH(CH₂)₃Si(O-)(O-)(O—solid support) | CH(CH₃)-CONH-(3,5-dimethylphenyl), CONH-pyrrolidine(N-CH₃) | —Cl |

Figure 5l

| Sample | Z | X | Y |
|---|---|---|---|
| FSC 19 | —NH—(CH$_2$)$_2$—NHCO—CH—NHCO—(3,5-dinitrophenyl), with CH$_2$—CH(CH$_3$)$_2$ side chain | —NH—(CH$_2$)$_2$—NHCO—CH—NHCO—(3,5-dinitrophenyl), with CH$_2$—CH(CH$_3$)$_2$ side chain | —NH(CH$_2$)$_3$Si(O—)$_3$—solid support |
| FSC 20 | —NH—(CH$_2$)$_2$—NHCO—CH(Ph)—NHCO—(3,5-dinitrophenyl) | —NH—(CH$_2$)$_2$—NHCO—CH(Ph)—NHCO—(3,5-dinitrophenyl) | —NH(CH$_2$)$_3$Si(O—)$_3$—solid support |
| FSC 21 | —NH—(CH$_2$)$_2$—NHCO—CH(CH$_3$)—NHCO—(3,5-dinitrophenyl) | —NH—(CH$_2$)$_2$—NHCO—CH(CH$_3$)—NHCO—(3,5-dinitrophenyl) | —NH(CH$_2$)$_3$Si(O—)$_3$—solid support |

Figure 5m

| Sample | Z | X | Y |
|---|---|---|---|
| FSC 22 | —Cl | cyclohexane-NH— with NHCO-(3,5-dinitrophenyl) | —NH(CH₂)₃Si(O-)₃–solid support |
| FSC 22 | —NH(CH₂)₃Si(O-)₃–solid support | cyclohexane-NH— with NHCO-(3,5-dinitrophenyl) | —Cl |
| FSC 23 | —Cl | cyclohexane-NH— with NHCO—CH(CH₃)-(6-methoxynaphthyl) | —NH(CH₂)₃Si(O-)₃–solid support |

Figure 5n

| Sample | Z | X | Y |
|---|---|---|---|
| FSC 23 | —NH(CH₂)₃Si—(O)₃—solid support | —NH—cyclohexyl-NHCO—CH(CH₃)—(6-methoxynaphthalen-2-yl) | —Cl |
| FSC 24 | —NH—(CH₂)₂—NHCO—CH(CH₂Ph)—NHCO—(3,5-dinitrophenyl) | —NH—(CH₂)₂—NHCO—CH(CH₂Ph)—NHCO—(3,5-dinitrophenyl) | —NH(CH₂)₃Si—(O)₃—solid support |

Figure 5o

Figure 5p

CHIRAL STATIONARY PHASES FOR ENANTIOMERS SEPARATION AND THEIR PREPARATION

This appln is a 371 of PCT/EP99/02869 filed on Jun. 28, 1999.

STATE OF THE ART

The separation of enantiomers by means of liquid chromatography (LC) using chiral stationary phases is based on the reversible diasteromeric association between the chiral environment in the column and the enantiomers in the solution (S. Allenmark, "Chromatographic Enantioseparation", 2nd Edition, Ellis Horwood, N.Y., 1991, pp. 1007–1008).

The chiral stationary phases for LC are normally classified on the basis of their general structures. One group is based on either synthetic or natural polymers and is totally or intrinsically chiral.

Another group is made up of chiral selectors with a low molecular weight bound to a solid, incompressible, matrix, generally silica. The latter provides remarkable advantages with respect to the former since the chiral selectors can be designed rationally (K. B. Lipkowitz, Modelling Enantiodifferentiation in Chiral Chromatography, in "A Practical Approach to Chiral Separation by Liquid Chromatography", G. Subramanian Editor, VCH, Weinheim, 1994, pp. 19–55).

This implies that they can be selected on a rational basis; in fact, their enantioselective features can often be evaluated by means of NMR studies or can be singled out thanks to computer modelling according to the various types of chemical interactions.

Among the most frequently used chiral selectors bound to a solid support it is worth quoting the "crown ethers" (E. P. Kyba et al., *J. Am. Chem. Soc.,* 1978, 100: 4555–4568), the charge-transfer complexes (W. H. Pirkle et al., *J. Am. Chem. Soc.* 1986, 108: 352) the chiral selectors based on hydrogen bonds (see e.g. S. Hara et al., *J. Chromatogr.,* 1979, 186: 543) and other types of chiral selectors (P. Salvadori et al., *Tetrahedron,* 1987, 43, 4969).

All these products exhibit some limitations with respect to their enantioseparating ability, which are due either to the high number of functional groups or structural subunits that participate in the interaction with the enantiomers in solution.

The range of application of chiral selectors should therefore be widened up so as to promote the use and versatility of chromatography based on stationary chiral phases.

Is a fungicide widely used in agriculture; some of its derivatives such as glutathione are described in Tetrahedron, 1995, 51: 2331. None of these derivatives is used in chromatography.

FIELD OF THE INVENTION

This invention relates to new derivatives of 1,3-dicyano-2,4,5,6,-tetrachlorobenzene containing one or more chiral groups and one group acting as a spacer. The stationary phases obtained from these derivatives provide an efficient separation of enantiomers.

SUMMARY

The present invention describes new chiral stationary phases, and the optically active compounds therein contained. The optically active compounds contained in the stationary phases are represented by the formula of structure (I), which comprise at least one asymmetric carbon atom and a substituent acting as a spacer. The stationary phases of the present invention can be used in the preparation of chromatographic columns useful for the analytical and preparative separation of enantiomers.

BRIEF DESCRIPTION OF THE FIGS.

FIG. 1: preparation of the FSC 1 chiral stationary phase

Figure 2:
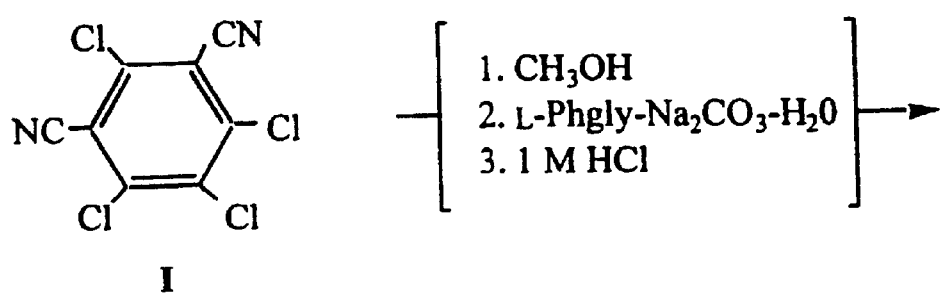
Figure 2:
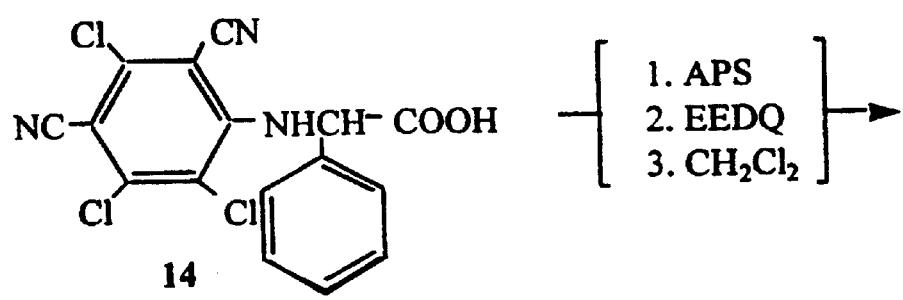
Figure 2:
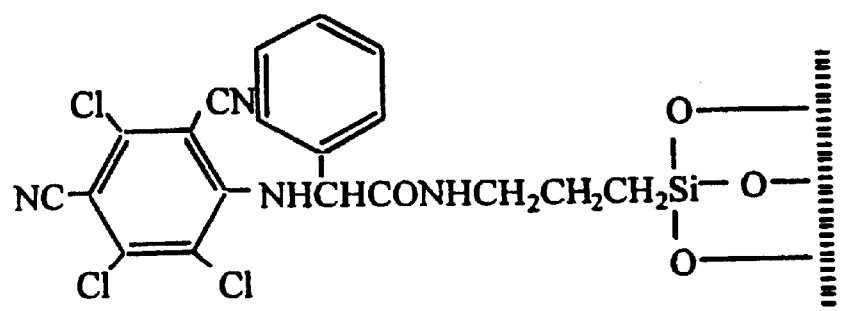

FIG. 2: preparation of the FSC 5 chiral stationary phase

Figure 3:
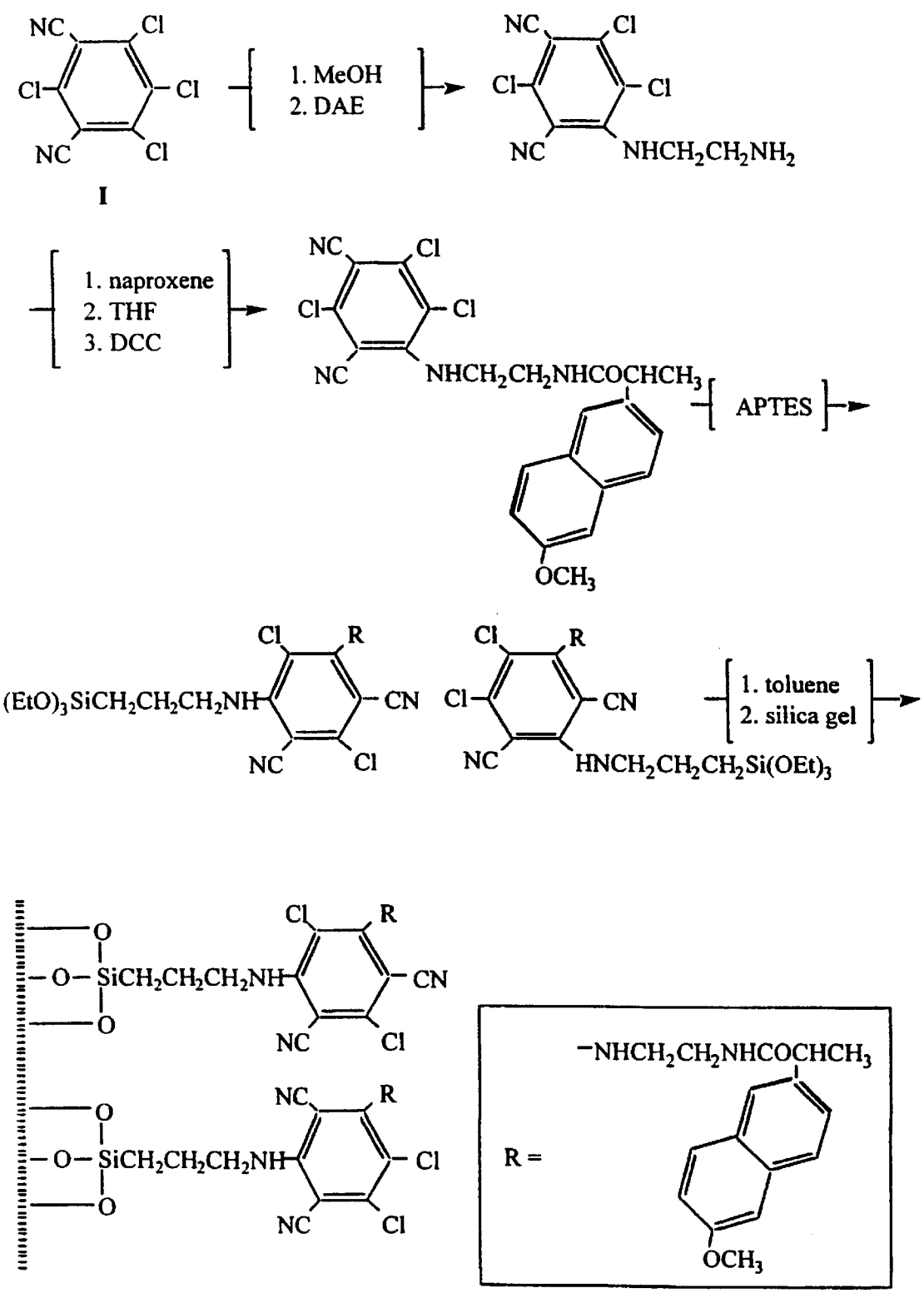

FIG. 3: preparation of the FSC 10 chiral stationary phase

Figure 4:
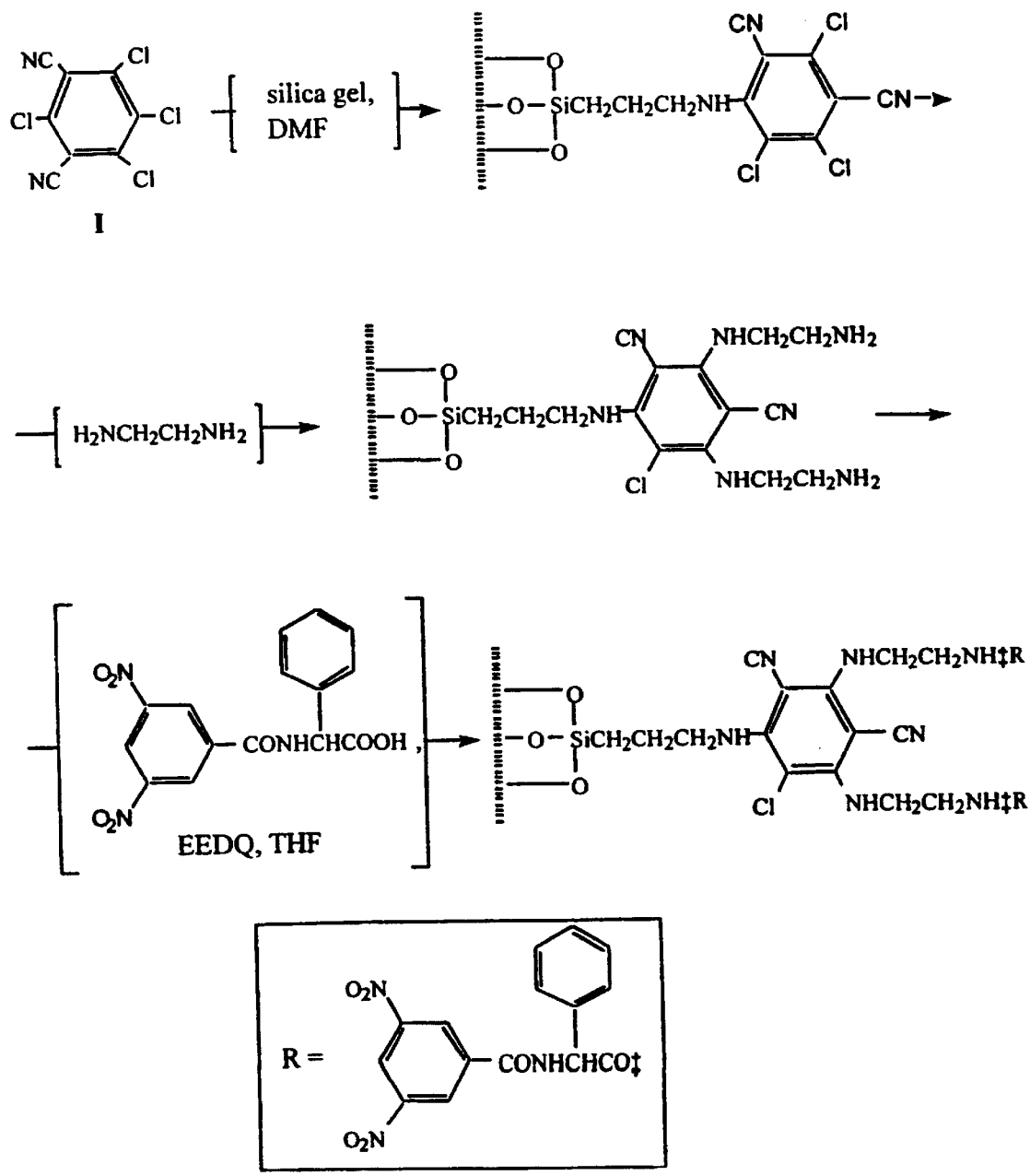

FIG. 4: preparation of the FSC 20 chiral stationary phase

Figure 5E:
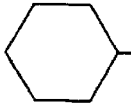
Figure 5E:
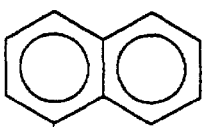
Figure 5E:
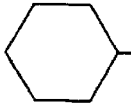
Figure 5E:
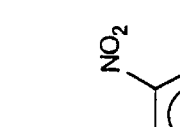
Figure 5F:
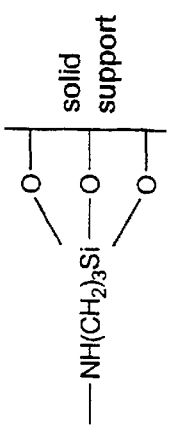
Figure 5F:
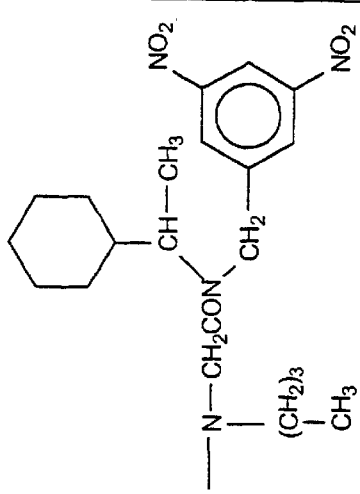
Figure 5F:
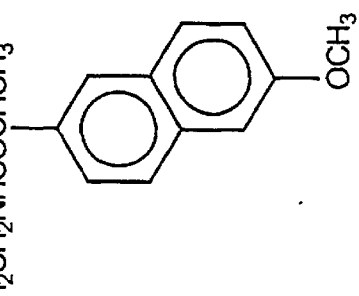
Figure 5F:
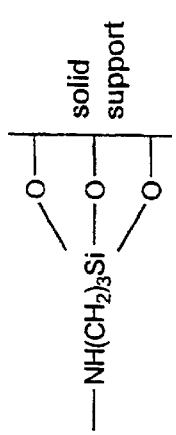
Figure 5O:
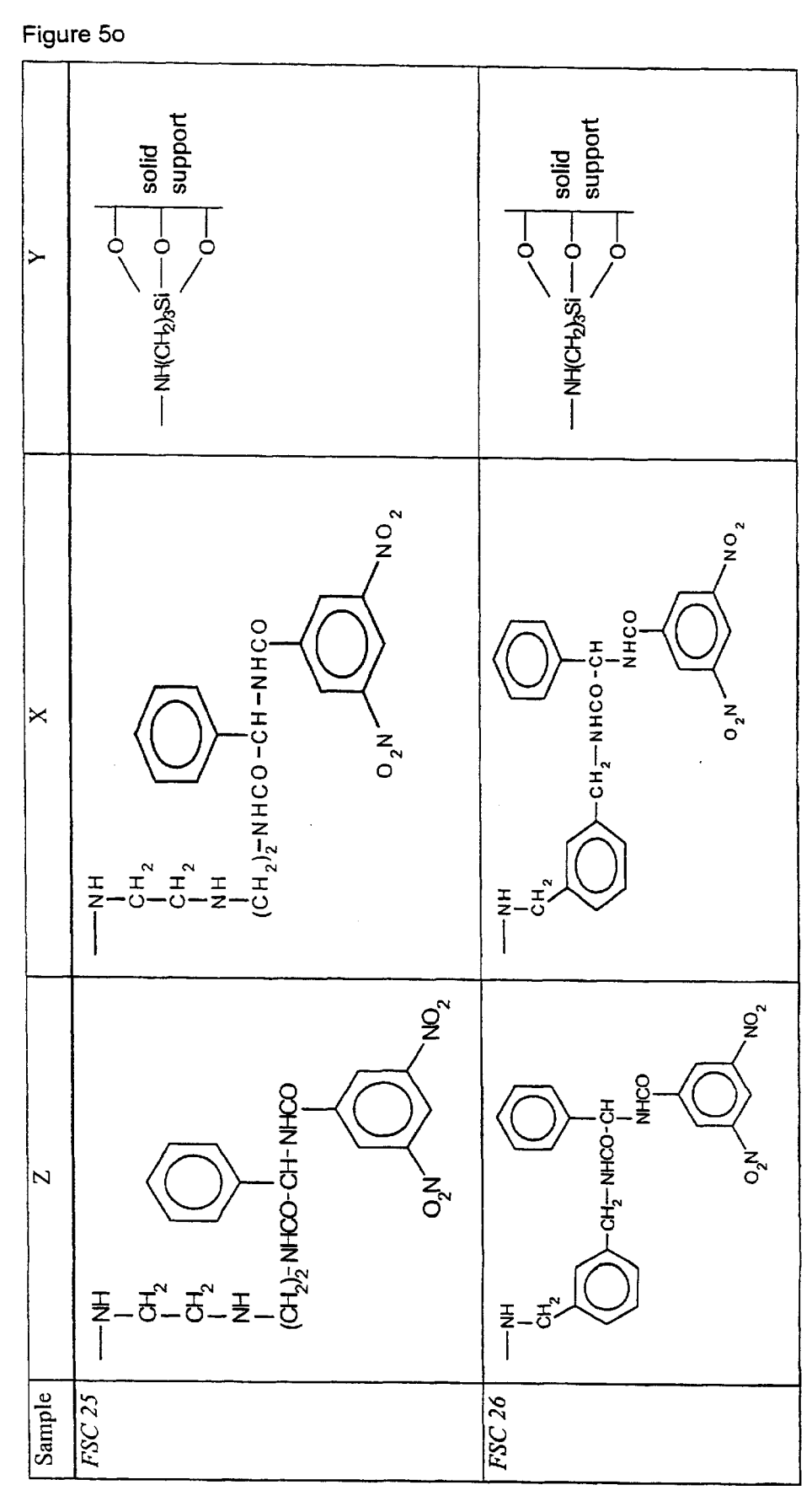
Figure 5P:
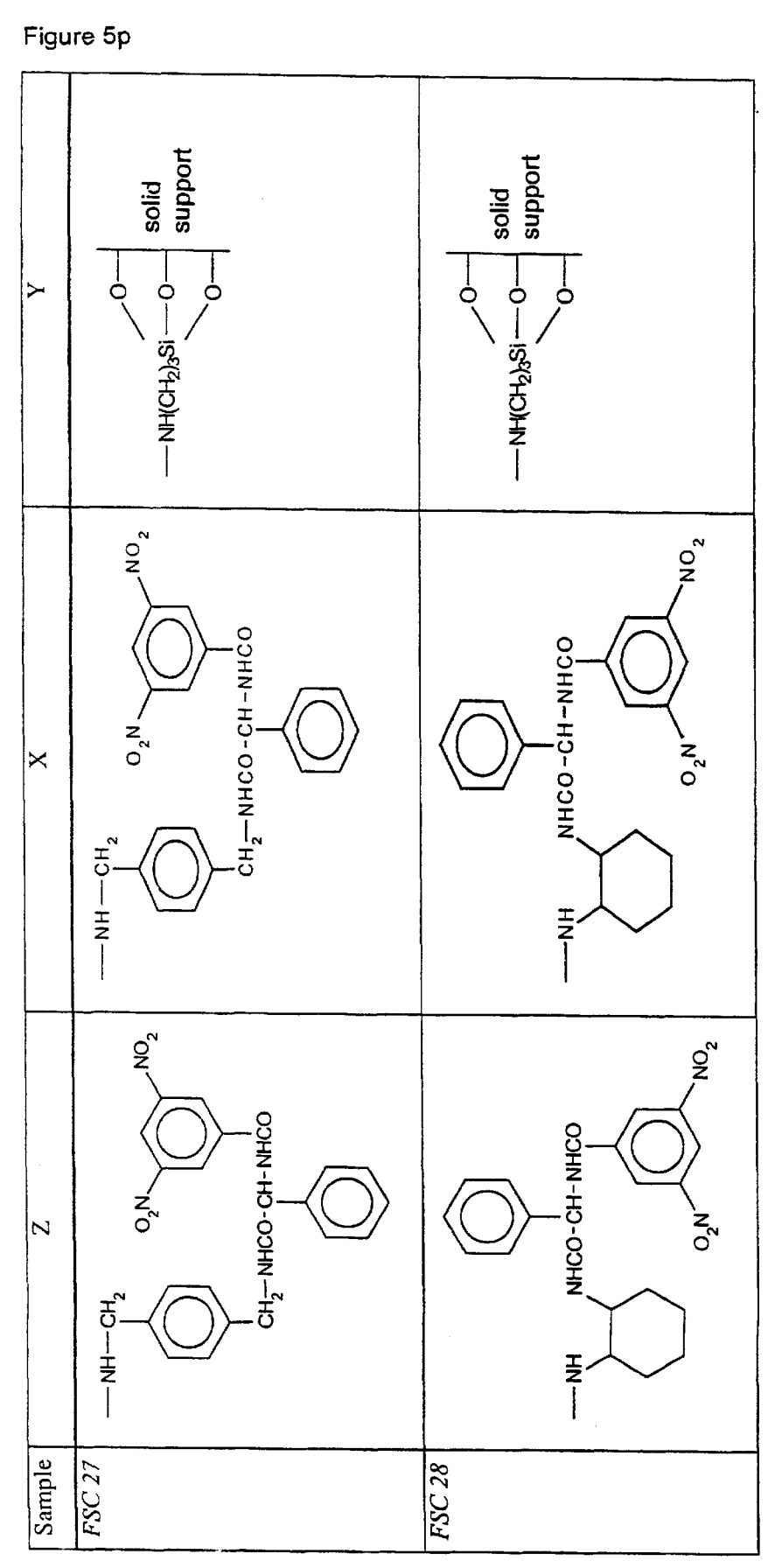

FIG. 5a–p: Z, X and Y substituents of the chiral stationary phases (1)–(28) as prepared in the experimental part. The reference structure is that of formula (I).

Figure 6:
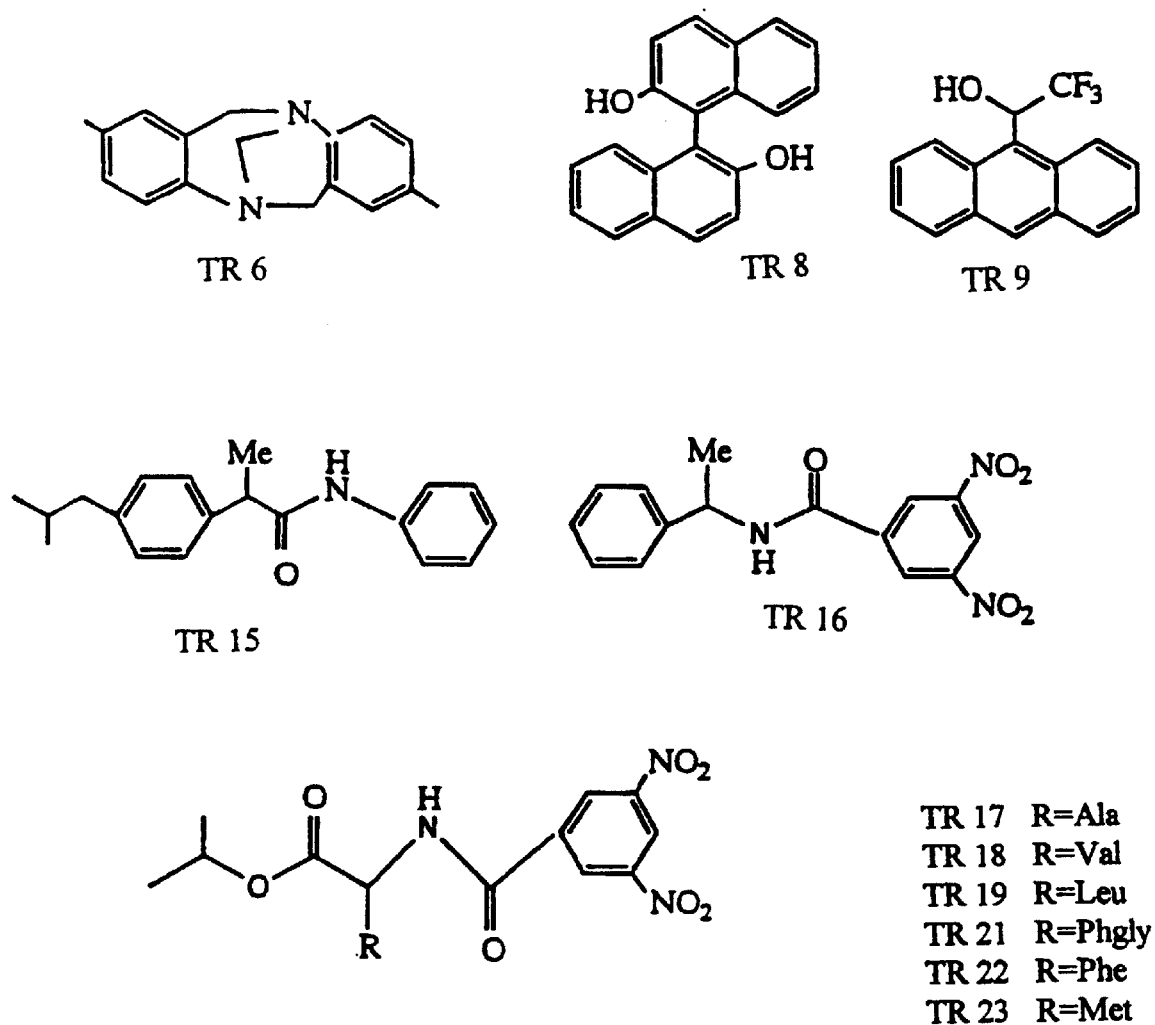

FIG. 6: list of racemic mixtures

DETAILED DESCRIPTION OF THE INVENTION

The present invention regards chiral stationary phases for chromatography based on new chiral derivatives, hereinafter referred to as "chiral selectors".

The chiral selectors, that form the first object of the present invention are represented by the general formula (I):

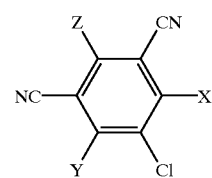

where:
$X = NR_1 - CHR_2R_3$ $R_1$ represents H, alkyl $C_1$–$C_6$ linear or branched, $R_2$ represents H, alkyl $C_1$–$C_6$ linear or branched, aryl or arylalkyl possibly containing an heteroatom, being said aryl or arylalkyl optionally substituted with —OH, —$CH_2CONH_2$, $R_3$ represents:

alkyl $C_1$–$C_6$ linear or branched, $(CH_2)_p$—COOH, $(CH_2)_p$—CONH$_2$, $(CH_2)_p$—CONHR$_4$, $(CH_2)_p$—NHCOR$_4$, $(CH_2)_p$—CON(R$_4$R$_5$), CONHCH(R$_4$) CONHR$_4$, $(CH_2)_p$—NHCOCH(R$_4$)NHCOR$_4$, $C_6H_4$—$CH_2$—NHCOCH(R$_4$)NHCOR$_4$, $CH_2NH(CH_2)_p$—NHCOCH(R$_4$)NHCOR$_4$ where p is an integer from 0 to 4, $R_4$ and $R_5$ independently of each other represent (a) alkyl $C_1$–$C_6$ linear or cyclic, (b) aryl, (c) a spacer group of formula $(CH_2)n$—Si—$(OR_6)_3$ where n is comprised between 1 and 10 and $R_6$ represents an alkyl $C_1$–$C_4$; said groups (a) and (b) are optionally substituted with alkyl $C_1$–$C_4$, aryl, cycloalkyl $C_5$–$C_6$, NO$_2$, OCH$_3$, or:

(i) $R_1$ forms together with $R_2$, with the carbon atom bound to $R_2$ and with the nitrogen, a 5–6 membered ring, or (ii) $R_2$ forms with $R_3$ and with the carbon atom bound to $R_2$ and $R_3$ a 5–6 membered ring substituted by —NHCOR$_4$, or by —NHCOCH(R$_4$)NHCOR$_4$, $R_4$ being as above defined;

Y e Z independently of each other represent: chloro, X group where X has the meanings given above, a spacer group of formula —A(CH$_2$)n-Si—(OR$_6$)$_3$ where A represents NH or O, preferably NH, and n and R$_6$ have the meanings given above; with the proviso that said formula (I) contains: (a) one to three X groups containing at least one chiral atom, and (b) only one spacer group as above defined.

Generally, in formula (I), the X group represents preferably an α-aminoacid, ester of aminoacid, amide of aminoacid, arylalkylalcohol, arylcarboxylic acid, arylcarboxylic acid ester, arylcarboxylic acid ester, aminoamide, arylalkylamine. The arylalkyl groups quoted above are preferably represented by the benzyl group.

The aryl groups are preferably represented by either phenyl or naphthyl. The derivatives of formula (I) always contain at least one chiral carbon atom. This carbon atom is always contained in the X group and is normally represented by the carbon C* of the C*HR$_2$R$_3$ group or it is contained in the R$_3$ substituent. Within the formula (I) herein defined, it is possible to identify subgroups of products particularly useful for the purpose of this invention.

A first group of selectors preferred is represented by formula (I) where:
R$_1$ represents H, alkyl C$_1$–C$_6$ linear or branched, R$_2$ represents H, alkyl C$_1$–C$_6$ linear or branched, aryl, arylalkyl, CH$_2$CONH$_2$, or R$_1$ forms with R$_2$, with the carbon atom bound to R$_2$ and with N a 5–6 membered ring; R$_3$ represents alkyl C$_1$–C6 linear or branched, (CH$_2$)$_p$—CONHR$_4$, (CH$_2$)$_p$—CON(R$_4$R$_5$), where p, R$_4$ and R$_5$ have the meanings given above.

A second group of selectors preferred is represented by formula (I) where:
R$_1$ represents H, R$_2$ represents: H, R$_3$ represents (CH$_2$)$_p$—NHCOR$_4$, CH$_2$—NHCOR$_4$, where p, R$_4$ have the meanings given above; or R$_2$ forms with R$_3$ and the carbon atom bound to R$_2$ and R$_3$ a 5–6 membered ring.

A third group of preferred selectors is represented by formula (I) where:
R$_1$ represents H, R$_2$ represents H, or R$_2$ forms with R$_1$, with the carbon atom bound to R$_2$ and with N a 5–6 membered ring; R$_3$ represents CONHCH(R$_4$) CONHR$_4$, where p, R$_4$ have the meanings given above.

A fourth group of selectors preferred is represented by formula (I) where:
R$_1$ represents H, R$_2$ represents H, , R$_3$ represents:, (CH$_2$)$_p$—NHCOCH(R$_4$)NHCOR$_4$, C$_6$H$_4$—CH$_2$—NHCOCH (R$_4$)NHCOR$_4$, CH$_2$NH(CH$_2$)$_p$—NHCOCH(R$_4$) NHCOR$_4$; or R2 forms with R3 and with the carbon atom bound to R2 and R3 a 5–6 membered ring substituted with NHCOCH(R$_4$)NHCOR$_4$ ; p and R$_4$ having the meanings given above.

Preferred selectors of formula (I) are quoted in the following list. The names in bracket refer to the corresponding chiral stationary phases whose structure are reported in FIG. 5:

5-Chloro-4,6-di-[R-1-(naphth-1-yl)ethyl]amino-2-(3-trimethylsilylpropyl)amino-1,3-dicyanobenzene (FSC 1)

4-[(3,5-dimethylanilido)-L-phenylalaninyl]-6-(3-triethoxysilyl)propylamino-2,5-dicloro-1,3-dicyanobenzene, and 4-[(3,5-Dimethyanilido)-L-phenylalaninyl]-2-(3-triethoxysilyl)propylamino-5,6-dicloro, 1,3-dicyanobenzene (FSC 3)

4-[(naphth-1-yl)amido)-L-phenylalaninyl]-2-(3-triethoxypropyl)amino-5,6-dichloro-1,3-dicyanobenzene and 4-[(Naphth-1-yl)amido)-L-phenylalaninyl]-6-(3-triethoxypropyl)amino-2,5-dichloro-1,3-dicyanobenzene (FSC 4)

4-[R-1-(naphth-1-yl)ethyl]amino-2-(3-triethoxysilylpropyl) amino-5,6-dichloro-1,3-dicyanobenzene and 4-[R-1-(naphth-1-yl)ethyl]amino-6-(3-triethoxysilylpropyl) amino-2,5-dichloro-1,3-dicyanobenzene (FSC 6)

4-{n-butyl-[R-1-(naphth-1-yl)ethyl]acetamido}amino-6-(3-triethoxysilylpropyl)amino-2,5-dichloro-1,3-dicyanobenzene, and 4-{n-butyl-[R-1-(naphth-1-yl)ethyl] acetamido}amino-2-(3-trimethylsilylpropyl)amino-5,6-dichloro -1,3-dicyanobenzene (FSC 7)

4-{n-butyl-[R-1-(cyclohexyl)ethyl-N-R-(naphth-1-yl) methyl]acetamido}amino-6-(3-triethoxysilylpropyl) amino-2,5-trichloro-1,3-dicyanobenzene and 4-{n-butyl-[R-1-(cyclohexyl)ethyl-N-R-(naphth-1-yl)methyl] acetamido}amino-2-(3-triethoxysilylpropyl)amino-5,6-trichloro-1,3-dicyanobenzene (FSC 8)

4-{n-butyl-[N-R-1-(cyclohexyl)ethyl-N-3,5-dinitrobenzyl] acetamido}amino-6-(3-triethoxysilylpropyl)amino-2,5-dichloro-1,3-dicyanobenzene and 4-{n-butyl-[N-R-1-(cyclohexyl)ethyl-N-3,5-dinitrobenzyl] acetamido}amino-2-(3-triethoxysilylpropyl)amino-5, 6trichloro-1,3-dicyanobenzene (FSC 9)

4-{2-[2-(6-methoxy-naphth-2-yl)-propionylamido] ethyl}amino-6-(3-triethoxysilylpropyl)amino-2,5-dichloro-1,3-dicyanobenzene and 4-{2-[2-(6-methoxy-naphth-2-yl)-propionylamido]ethyl}amino-2-(3-triethoxysilylpropylamino -5,6-dichloro-1,3-dicyanobenzene (FSC 10)

4-{methyl-[R-1-(naphth-1-yl)ethyl]acetamido}amino-2-(3-triethoxysilylpropyl)amino-5,6-dichloro-1,3-dicyanobenzene, and 4-{methyl-[R-1-(naphth-1-yl)ethyl] acetamido}amino-6-(3-trimethylsilylpropyl)amino-2,5-dichloro -1,3-dicyanobenzene (FSC 11)

4-[3,5-dimethylanilido)-L-alaninyl]-2,5-dichloro-6-(3-triethoxysilylpropyl)amino-1,3-dicyanobenzene, and 4-[3,5-dimethylanilido)-L-alaninyl]-5,6-dichloro-2-(3-triethoxysilylpropyl)amino-1,3-dicyanobenzene (FSC 14)

4-(cyclohexylamido-L-alaninyl)-2,5-dichloro-6-(3-triethoxysilylpropyl)amino-1,3-dicyanobenzene, and 4-(cyclohexylamido-L-alaninyl)-5,6-dichloro-2-(3-triethoxysilylpropyl)amino-1,3-dicyanobenzene (FSC 15)

4-[(3,5-dimethylanilido)-prolinyl]-2,5-dichloro-6-(3-triethoxysilylpropyl)amino-1,3-dicyanobenzene, and 4-[(3,5-dimethylanilido)-prolinyl]-5,6-Dichloro-2-(3-triethoxysilylpropyl)amino1,3-dicyanobenzene (FSC 16)

4-(prolinyl-cyclohexylamide)-2,5-dichloro-6-(3-triethoxysilylpropyl)amino-1,3-dicyanobenzene, and 4-(prolinyl-cyclohexylamide)-5,6-dichloro-2-(3-triethoxysilylpropyl)amino-1,3-dicyanobenzene (FSC 17)

4-[L-prolinyl-L-alanilyl-(3,5-dimethylanilide)]-2,5-dichloro-6-(3-triethoxysilylpropyl)amino-1,3-dicyanobenzene, and 4-[L-prolinyl-L-alanilyl-(3,5-dimethylanilide)]-2,5-dichloro-2-(3-triethoxysilylpropyl) amino-1,3-dicyanobenzene (FSC 18)

4-{[2-(3,5-dinitrobenzoyl)-cyclohexyl]amide}-2,5-dichloro-6-(3-triethoxysilylpropyl)amino-1,3-dicyanobenzene, and 4-(2-(3,5-dinitrobenzoyl)-cyclohexyl]amide)amino-5,6-dichloro-2-(3-triethoxysilylpropyl)amino-1,3-dicyanobenzene (FSC 22)

4-{2-[2-(6-methoxy-naphth-2-yl)-propionylamido] cyclohexyl}amino-6-(3-triethoxysilylpropyl)amino-2,5-dichloro-1,3-dicyanobenzene and 4-{2-[2-(6-methoxy-naphth-2-yl)-propionylamido]cyclohexylamino-2-(3-triethoxysilylpropyl)amino-5,6-dichloro-1,3-dicyanobenzene (FSC 23)

Formula (I) entails the presence of at least one X chiral substituent bound in meta position with respect to the Z group. When Y=X, formula (I) can contain two chiral groups in meta position with respect to the Z group, by conferring thus specific symmetry characters: if the two X substituents are structurally and stereochemically different from one another, the molecule acquires C1 symmetry; on the other side if the two X substituents are structurally and stereochemically identical, the molecule acquires C2 symmetry. Another possibility of having a chiral selector of formula (I) with two chiral groups on the tetrachlorodicyanobenzene is allowed when Z=X.

Formula (I) always contains one spacer group as above defined. Preferred spacer groups are those where $R_6$ represents ethyl and n is 3. A most preferred spacer is the (3-triethoxylsilylpropyl)amino group. As evident from formula (I), the spacer group can be indifferently present as an Y, Z group or as a further substituent of the chiral group. In this latter case (i.e. when the spacer is defined by the substituent $R_4$ or $R_5$, option (c)), the $R_3$ substituents are preferably chosen among: $(CH_2)_p$—$CONHR_4$, $(CH_2)_p$—$CON(R_4R_5)$, $CONHCH(R_4) CONHR_4$. By means of a covalent binding that involves the oxygen atoms of the $(OR_6)_3$ groups, the spacer group allows to bind the molecule of formula (I) to a solid support and to form chiral stationary phases for chromatography. The linkage that forms can be represented in this way:

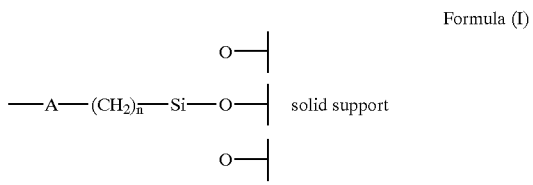

Formula (I)

The solid support can be of either of organic or, preferably, inorganic type. Suitable examples of solid inorganic support are silica gel, alumina, kaolin, titanium oxide, magnesium, silicate, synthetic polymers. The preferred solid support is silica (e.g. silica gel).

The present invention relates also to a process for the production of chiral stationary phases. This process entails the use of 1,3-dicyano-2,4,5,6-tetrachlorobenzene as a reagent; as mentioned above, this product is commercially available.

In agreement with the structural requirements of formula (I), the present process entails the introduction of only one spacer group, and from one to three chiral X groups.

The process is thus characterised by comprising the following separate reaction steps which can take place in any order:

introduction of one or more chiral X groups on the dicyanobenzene ring, introduction of the spacer group either on dicyanobenzene ring or on a chiral group already present on the dicyanobenzene ring, formation of covalent linkage between the spacer group and a solid support.

According to a first specific embodiment, the above described process comprises the following steps:
a) introduction of one or more chiral X groups on the 1,3-dicyano-2,4,5,6-tetrachlorobenzene by substitution of one or both chlorine atoms in position 4 or 6 with the obtainment of chiral derivatives of formula (II).

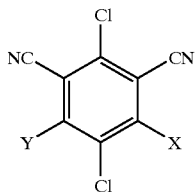

Formula (II)

where X and Y have the meanings defined above, with the only difference that they do not contain any spacer group.
b) introduction of a spacer group in the derivative of formula (II) obtained in step a), wherein said spacer group is introduced either by substitution of one chlorine atom on the dicyanobenzene ring or it is introduced on the X group, with the obtainment of the chiral selector of formula (I).
c) formation of covalent linkage between the spacer group and the solid support with the obtainment of the chiral stationary phase.

According to a second specific embodiment, the above described process comprises the following steps:
a) introduction of one or more chiral X groups on the 1,3-dicyano-2,4,5,6-tetrachlorobenzene by substitution of one or both chlorine atoms in position 4 or 6 of the dicyanobenzene ring with the obtainment of chiral derivatives of formula (II).
b) formation of covalent linkage between a spacer group and a solid support.
c) introduction of the spacer group linked to the solid support obtained in step b) either on position 2 or 4 or 6 of the dicyanobenzene ring or on the X group of chiral selector of formula (II) obtained in a) with the obtainment of the chiral stationary phase.

According to a third specific embodiment, the above described process comprises the following steps:
a) introduction of a spacer group on 1,3-dicyano-2,4,5,6-tetrachlorobenzene by substitution of one chlorine atom in position 4 or 6 of the dicyanobenzene ring, where said spacer group is possibly previously bounded to the solid support
b) introduction of one or more chiral X groups on the dicyanobenzene ring by substitution of either one or both chlorine atoms in position 2 or 4 or 6 of the compound of step a), possibly formation of covalent linkage between the spacer group and the solid support, with the obtainment of chiral stationary phases.

The chiral X groups are introduced in the 1,3-dicyano-2,4,5,6-tetrachlorobenzene by substitution of one or more of the chlorine atoms in position 2,4,6, using suitable reagents containing the X group.

Examples of these reagents are α-aminoacids, α-arylalkyl amine, secondary alcohols, amides or esters of chiral carboxylic acids. Examples of specific reagents are: 1-phenylethylamine, proline, (1-(naphth-1-yl)ethylamine, phenylalanine, phenylglycine, n-butylamine, naphthylethylamine, 3,5-dimethylaniline, cyclohexylethylamine, sarcosine, asparagine.

The spacer group is preferably introduced by reaction with a reagent of formula AH—$(CH_2)$n-Si—$(OR_6)_3$ where A=$NH_2$, OH, and where n and $R_6$ have the meanings described above.

The introduction of X, Y and Z groups is performed by heating the reagents in a suitable solvent, possibly in the presence of an excess of this solvent. The operational temperature ranges from 20° C. to 150° C. and the reaction time ranges from 60 minutes to 80 hours. When a single X group is introduced in the ring, then the reaction is preferably performed in a polar solvent or in a mixture of solvents. Moreover the times are shorter, ranging from 1 to 5 hours. In case derivatives with two X substituents are to be prepared then it is preferable to use an excess of liquid reagent (molar excess 50–100 times) and then carry on heating up to 80 hours.

The X chiral groups that are present in the stationary phases that are the object of this invention are in an optically pure form, that is they have a specific stereochemical configuration. The synthesis of the products of formula (II) and (I) that are the object of the present invention are carried out by using the nucleophylic reagents containing the X group in an optically pure form.

The covalent binding between the spacer group and the solid support is obtained according to known chemical reactions comprising heating at high temperature in the presence of an organic solvent.

The preparation of the chiral stationary phases based on chiral selectors of formula (I), and the specific structures of some chiral stationary phases are shown in FIGS. 1–5.

FIG. 1,2,3,4 show the preparation of stationary chiral phases called FSC 1, 5, 10, 20. The experimental part reports the preparation of stationary phases starting from a variety of chiral selectors of formula (I).

The stationary phases (whose structures are illustrated in FIG. 5) that are the object of the present invention allow the separation of several racemic mixtures of commercial interest. The use of these chiral stationary phases for the enantiomeric separation by chromatography, and in particular their use in the preparation of high performance liquid chromatographic columns (HPLC) constitutes a further aspect of the present invention. Moreover, the present invention comprises a method of separation of enantiomeric mixtures by means of such chiral stationary phases. Examples of isomer separation by means of stationary phases object of the invention are reported in the experimental part.

The stationary phases which are object of the present invention allow both the analytical and preparative separation of enantiomers of structurally different compounds and to determine the enantiomeric composition obtained by means of various asymmetric syntheses (V. Vinkovic et al., Tetrahedron, 1997, 53, 689; E. Ljubovic, et al. *Tetrahedron: Asymm.*, 1997, 8,1).

The separation process takes place by means of several efficient interactions for the enatioselection and also by means of new kinds of cumulative interaction that can be performed specifically and only by means of the selectors of formula (I) claimed in the present invention. In particular, the high electronegativity of the chlorine atom and the dipolar moment of the CN group of the chiral selector promotes the setting of polar interactions and the formation of hydrogen bonds with the enantiomers to be separated.

Moreover, the lack of π electrons on the aromatic ring that is measured with the sum of the σ constants of each substituents (chlorine, cyano- amino, amido, alkoxy) is higher than the one calculated for the amide derivative of N-(3,5-dinitrobenzoyl)-aminoacid used by Pirkle as a chiral selector (Pirkle, *J. Am. Chem. Soc.* 1986, 108, 352). The new stationary phases are therefore remarkably more effective in the formation of interactions of the π-π kind with strong π-donor groups present in the chiral compounds to be separated. In particular, the stationary phases claimed turned out to be effective in the separation of a wide number of enantiomers such as α-aminoacids and of their derivatives with N- and O-protection, carboxylic acids and their esters or heterocyclic or acyclic amides, amines, alcohols, thiols, epoxides and aziridines.

The examples listed hereunder aim at illustrating the invention without a limitative purpose.

EXAMPLES

Examples of Preparation of Chiral Selectors and Stationary Phases

Example 1

5-Chloro-4,6-di-[R-1-(naphth-1-yl)ethyl]amino-2-(3-triethoxysilylpropyl)amino-1,3-dicyanobenzene The mixture of 2,4,5,6-tetrachloro-1,3-dicyanobenzene (2.0 g; 7.5 mmol) and [R-1-(naphth-1-yl)ethyl]amine (5.13 g; 30.0 mmol) is heated at 100° C. in DMF (30 ml) for 48 hr. Then the solvent is evaporated to dryness, the crude product dissolved in toluene and purified by chromatography on silica gel column (100 g), using toluene as eluent. It is obtained 3.78 g (93%) of slightly yellow crystals of the pure product: 2,5-dichloro-4,6-di-[R-1-(naphth-1-yl)ethyl] amino-1,3-dicyanobenzene. The analysis of this product is as follows: Anal. calcd. for $C_{32}H_{24}N_4Cl_2$: C, 71.77; H, 4.51; and N, 10.4. Found: C, 71.72; H, 4.56; and N, 10.42%.

This compound (3.28 g, 6.13 mmol) in excess of 3-aminopropyltriethoxysilane (10.0 ml, 42.5 mmol) is heated at 110° C. for 24 hrs. The solution is cooled to room temperature, diluted with toluene, applied on to flash chromatography column with silica gel and eluted with toluene. The pure product (3.85 g, 87%) is isolated as pale-yellow oil.

IR (KBr): 3400, 3060, 2980, 2920, 2200, 1590, 1510, 1470, 1450, 1390, 1380, 1360, 1300, 1260, 1230, 1200, 1160, 1100, 1080, 1010, 950, 860, 800, 780, 720 cm$^{-1}$.

Anal. calcd. for $C_{41}H_{46}N_5SiO_3Cl$ (720.36); C, 68.35; H, 6.43; N, 9.72; Found; C, 68.31; H, 6.48; N, 9.68%.

Example 2

Chiral Stationary Phase FSC 1

The compound of example 1 (7.70 g; 10.6 mmol) and silica gel LiChrospher Si 100 (4.18 g) are heated under reflux in dry toluene over 72 hr. Chiral stationary phase FSC 1 (5.7 9) is isolated as pale-yellow amorphous material.

Analysis, found; C 17.81, H 2.00, N 2.77%. According to elemental analysis it is calculated that 0.21 mmol of the chiral selector is bound on 1.0 g of silica gel.

Example 3

4-N-L-Phenylglycinyl-2,5,6-trichloro-1,3-dicyanobenzene

To 2,4,5,6-tetrachloro-1,3-dicyanobenzene (4.0 g, 15.0 mmol) in MeOH (100 ml) is added to a warm solution of L-phenylglycine (4.55 g, 30.0 mmol) and sodium carbonate (3.18 g, 30.0 mmol) in water (100 ml). The reaction mixture is stirred and heated under reflux for 1.5 hr, then cooled and filtered. The filtrate is acidified by addition of 1 M HCl (50 ml), and the precipitated product is separated by filtration. It is washed with water and dried in vacuo at ambient temperature. Crystallisation from ethanol afforded 1.40 g (25%) of pure product, white powder.

IR (KBr): 3500, 3320, 2220, 1715, 1570, 1500, 1450, 1380, 1310, 1290, 1260, 1210, 1180, 1120, 1070, 1040, 1000, 960, 910, 860, 760, 720, 690 cm$^{-1}$.

Anal. calcd. for $C_{16}H_8N_3O_2Cl_3$ (380.60 g/mol): C, 50.48; H, 2.11; and N, 11.04. Found: C, 50.53; H, 2.36; and N, 10.86%.

Example 4

Chiral stationary phase FSC 5

A mixture of silica gel LiChrospher 100 $NH_2$ (2.00 g,1.4 mmol of $N_2$), chiral prepared in the Example 3, (0.628 g, 1.59 mmol) and EEDQ (0.39 g, 1.59 mmol) is stirred in dichloromethane (10 ml) at room temperature for 16 hr. After addition of methanol (50 ml) stirring is continued for 30 min. The stationary phase is then separated by filtration, is washed with methanol, then dried at 70° C. for 4 hr. 2.15 g of the stationary phase FSC 5 are obtained.

Anal. found: C 8.08%, H 1.05%, N 1.66%. The % of N reveals that 1.0 g of the stationary phase contains 0.39 mmol of chiral selector.

Example 5

4-{n-butyl-[R-1-(cyclohexyl)ethyl-N-R-(naphth-1-yl)methyl]acetamido}amino-2,5,6-trichloro-1,3-dicyanobenzene R-1-(Cyclohexyl)ethylamine (CEA) (1.59 g, 12.5 mmol) and 1-chloromethylnaphthalene (2.45 g, 12.5 mmol) are dissolved in methanol (5 ml). Triethylamine (5 ml) is added. Reaction solution is heated for 3 hr under reflux, then evaporated to dryness. The solid residue is dissolved in dichloromethane (50 ml). The organic solution is washed with 1M aq. sodium bicarbonate, then with water. It is filtered through cotton-plug and evaporated. It afforded the oily N-(naphth-1-yl)-R-1-(cyclohexyl)ethylamine (2.23 g, 65%). The amine (2.13 g, 8 mmol) is then dissolved in dichloromethane (25 ml) and triethylamine (0.81 g, 8.0 mmol) added. To this solution isochloroacetyl chloride (0.90 g, 9.0 mmol) in dichloromethane (25 ml) is added dropwise. After 1 hr stirring at ambient temperature reaction solution is washed with 1M aq. bicarbonate. The organic phase is filtered through a cotton-plug and evaporated leaving 2.70 g (98%) of N-chloroacetyl-N-(naphth-1-yl)methyl-R-cyclohexylamine. This product is dissolved in methanol (10 ml), then n-butanol (5 ml) is added, and the reaction solution is heated under reflux for 5 hr. On evaporation to dryness, the residual oil is dissolved in dichloromethane (50 ml), then it is washed with 1M bicarbonate and water, filtered and evaporated, affording an oily product (3.01 g, 99%). Said amine (2.79 g, 7.33 mmol) and 2,4,5,6-tetrachloro-1,3-dicyanobenzene (0.97 g, 3.65 mmol) are heated in acetonitrile (20 ml) under reflux for 2 hr. On evaporation to dryness, the residue is dissolved in toluene and purified by chromatography on silica gel (40 g), using first toluene then toluene/acetone (30:1) as eluent. On evaporation of the fractions containing the pure product, 1.70 g (76%) of the pure title compound are obtained.

IR (KBr): 3030, 2920, 2850, 2220, 1650, 1600, 1550, 1510, 1450, 1410, 1375, 1310, 1220, 1200, 1175, 1125, 1065, 980, 910, 800, 770, 730, 695, 650, 620 $cm^{-1}$.

Anal. calcd. for $C_{33}H_{35}N_4OCl_3$ (609.99 g/mol): C, 64.97; H, 5.78; and N, 9.18. Found: C, 65.01; H, 5.89; and N, 9.15%.

Example 6

4-{n-butyl-[R-1-(cyclohexyl)ethyl-N-R-(naphth-1-yl)methyl]acetamido}amino-6-(3-triethoxysilyspropyl)amino-2,5-trichloro-1,3-dicyanobenzene and 4-{n-butyl-[R-1-(cyclohexyl)ethyl-N-R-(naphth-1-yl)methyl]acetamido}amino-2-(3-triethoxysilylpropyl)amino-5,6-trichloro-1,3-dicyanobenzene The chiral selector (1.00 g, 1.63 mmol) prepared in the Example 5 and 3-aminopropyltriethoxysilane (APTES) (3.0 ml) are heated at 100° C. for 1 hr. The crude product is purified by chromatography on silica gel column (30 g) using first toluene then toluene/acetone (30:1) as eluent. On evaporation of fractions containing the product, 0.99 g (76%) of pure product are obtained, as a mixture of title isomers (3:1).

IR (KBr): 3400, 3340, 2960, 2920, 2720, 2200, 1650, 1570, 1510, 1460, 1440, 1410, 1390, 1360, 1340, 1300, 1260, 1220, 1200, 1160, 1100, 950, 890, 840, 790, 770, 680 $cm^{-1}$.

Anal. calcd. for $C_{42}H_{57}N_5SiO_4Cl_2$ (794.89 g/mol): C, 63.45; H, 7.22; and N, 8.81. Found: C, 63.49; H, 7.48; and N, 8.88%.

Example 7

Chiral Stationary Phase FSC 8

A mixture of isomers (0.90 g, 1.15 mmol) as prepared in the Example 6 and Nucleosil 100–5 (2.03 g) are heated under reflux in dry toluene (5 ml) for 20 hr. The silica gel is filtered off, is washed with cold toluene, and dried in vacuo at 70° C. for 4 hr. It is obtained 2.26 g of the chiral stationary phase FSC 8.

Anal found: C, 8.73%; H, 1.62%; and N, 1.46%. According on % of N it is calculated that 0.21 mmol of chiral selector is bound at 1 g of chiral stationary phase.

Example 8

4-{2-[2-(6-methoxy-naphth-2-yl)-propionylamido]ethyl}amino-2,5,6-trichloro-1,3-dicyanobenzene 2,4,5,6-Tetrachloro-1,3-dicyanobenzene (5.0 g, 18.8 mmol) and 1,2-diaminoethane (5.0 ml) are stirred in methanol (100 ml) for 1 h at ambient temperature. The precipitate is collected on filter and is washed with methanol, then acetone, affording 4.41 g (81%) of pure product as pale-yellow powder:4-(2-aminoethylamino)-2,5,6-trichloro-1,3-dicyanobenzene. This product is characterised as follows: Anal calcd. for $C_{10}H_7N_4Cl_3$ (289.54 g/mol): C, 41.47; H, 2.43; and N, 19.35. Found: C, 41.62; H, 2.46; and N, 19.23%.

2-(6-Methoxy-naphth-2-yl)-propionic acid (0.50 g, 2.17 mmol) is dissolved in THF (5.0 ml). To the solution DCC (0.45 g, 2.17 mmol) in THF (5.0 ml) is added and then the compound above prepared (0.63 g, 2.2 mmol) in dry THF (10 ml) is added. After 2 h stirring at ambient temperature reaction mixture is filtered through a cotton plug. The filtrate diluted with 2-propanol (50 ml) and evaporated to final volume of ca 10 ml. On cooling pure product is precipitated, on after washing with 2-propanol and drying 0.85 g (78%) of pure product are obtained.

IR (KBr): 3380, 3220, 3180, 3040, 2950, 2220, 1650, 1610, 1570, 1510, 1450, 1390, 1340, 1300, 1260, 1210, 1160, 1120, 1020, 950, 920, 890, 850, 810, 750 i 700 $cm^{-1}$.

Anal calcd. for $C_{24}H_{19}N_4O_2Cl_3$ (501.77 g/mol): C, 57.44; H, 3.81; and N, 11.16. Found: C, 57.38; H, 3.62; and N, 11.15%.

Example 9

4-{2-[2-(6-methoxy-naphth-2-yl)-propionylamido]ethyl}amino-6-(3-triethoxysilylpropyl)amino-2,5-dichloro-1,3-dicyanobenzene and 4-{2-[2-(6-methoxy-naphth-2-yl)-propionylamido]ethyl}amino-2-(3-triethoxysilylpropyl)amino-5,6-dichloro-1,3-dicyanobenzene The compound prepared in Example 8 (0.7 g, 1.39 mmol) and 3-aminopropyltriethoxysilane (3.0 ml) are heated at 100° C. bath temperature for 60 min. Purification by chromatography on silica gel column (35 g) with toluene as eluent afforded 0.92 g (96%) of the pure isomeric 1:1 product mixture.

IR (KBr): 3340, 2950, 2200, 1650, 1570, 1510, 1450, 1390, 1350, 1260, 1200, 1150, 1060, 960, 850 i 760 cm$^{-1}$.

Anal. calcd. for $C_{33}H_{41}O_5N_5Cl_2Si$ (686.68 gmol$^{-1}$): C, 57.71; H, 6.01; and N, 10.20. Found: C, 57.63; H, 5.98; and N, 10.28%.

Example 10

Chiral Stationary Phase FSC 10

A mixture of isomers (0.700 g; 1.01 mmol) as prepared in the Example 9 and Nucleosil 100–5 (1.69 g) are heated under reflux in dry toluene (5 ml) for 20 h. The modified silica gel is filtered off, washed with cold toluene, and dried in vacuo at 70° C. for 4 hr. 2 g of the chiral stationary phase FSC 10 are obtained.

Anal. found: C, 8.67%; H, 1.77% and N, 1.26%. According to the elemental analysis it is calculated that 0.18 mmol of chiral selector is bound at 1 g of chiral stationary phase.

Example 11

4-N-L-Asparagyl-2,5,6-trichloro-1,3-dicyanobenzene

To the suspension of 2,4,5,6-tetrachloro-1,3-dicyanobenzene (5.0 9; 18.8 mmol) in methanol (100 ml) a preheated solution of L-asparagine monohydrate (5.64 g; 37.6 mmol) and sodium carbonate (3.98 g; 37.60 mmol) in water (100 ml) are added. The reaction mixture is heated at reflux for 1.5 h and filtered. The filtrate is washed with dichloromethane (2×100 ml), the aq. layer acidified with 1 M HCl (50 ml) and the acidic solution extracted with dichloromethane (2×100 ml). The organic phase is washed with water, filtered, concentrated to 100 ml. After storage in the refrigerator for 2 hr the solid product is precipitated and collected on G-4 filter. 2.51 g (37%) of title product as white solid material are obtained.

IR (KBr): 3480, 3360, 3320, 2900, 2500, 2220, 1730, 1650, 1570, 1500, 1400, 1320, 1200, 1120, 850, 810 cm$^{-1}$.

Anal. calcd. for $C_{12}H_7N_4O_3Cl_3$ (361.56): C, 39.86; H, 1.9; and N, 15.49. Found: C, 39.92; H, 2.12; and N, 15.41%.

Example 12

Chiral Stationary Phase FSC 13

The suspension of example 11 (0.55 g, 1.52 mmol), silica gel LiChrospher 100 NH$_2$ (1.96 g; 1.40 mmol of N2), and EEDQ (0.37 g; 1.52 mmol) in dry THF (10 ml) are stirred at room temperature for 16 h. The product is collected on G-4 filter, washed with methanol and dried at 70° C. for 4 hr to afford 2.18 g of FSC 13.

Anal. found C, 8.95%; H 1.43%; N 1.78%. According to %N it is calculated that 1.0 g of chiral stationary phase contains 0.14 mmol of chiral selector.

Example 13

4-[L-prolinyl-L-alanilyl-(3,5-dimethylanilide)]-2,5,6-trichloro-1,3-dicyanobenzene N-Boc-L-alanine (2.77 g; 14.6 mmol) is transformed in 3,5-dimethylanilide by DCC (3.02 g, 14.6 mmol) promoted condensation with 3,5-dimethylaniline (1.77 g, 14.6 mmol), using dichloromethane as the solvent at ambient temperature. 1.78 g (63%) of the crude product are obtained. To 4-N-L-prolinyl-2,5,6-trichloro-1,3-dicyanobenzene (2.55 g; 7.4 mmol) dissolved in dichloromethane (15.0 ml) DCC (1.53 g, 7.4 mmol) in 10 ml dichloromethane is added, then a solution of 3,5-dimethylanilido-L-alanine (1.42 g; 7.4 mmol) in dichloromethane (15.0 ml). After 18 h stirring at ambient temperature the crude product is isolated on filtration on DC-urea and evaporation, then purified by chromatography on silica gel column using toluene-acetone (100:3) as eluent. It is obtained 1.95 g (50%) of the pure product as pale-yellow powder.

IR (KBr): 3380, 3300, 2980, 2920, 2880, 2220, 1660, 1610, 1550, 1520, 1440, 1350, 1260, 1210, 1170, 1140, 1060, 1000, 970, 920, 890, 840, 750, 730, 690 cm$^{-1}$.

Example 14

4-[L-prolinyl-L-alanilyl-(3,5-dimethylanilide)]-2,5-dichloro-6-(3-triethoxysilylpropyl)amino-1,3-dicyanobenzene, and 4-[L-prolinyl-L-alanilyl-(3,5-dimethylanilide)]-2,5-dichloro-2-(3-triethoxysilylpropyl)amino-1,3-dicyanobenzene The compound from Example 13 (0.81 g; 1.55 mmol) and 3-aminopropyltriethoxysilane (3.0 ml) are reacted and the pure product is isolated by purification on silica gel column (30 g) by elution with toluene-acetone (20:1). 0.79 g (72%) of the mixture of the title isomers (1:1) are obtained.

IR (KBr): 3360, 2980, 2920, 2880, 2200, 1650, 1610, 1570, 1520, 1450, 1390, 1350, 1300, 1260, 1220, 1160, 1080, 950, 840, 780 i 690 cm$^{-1}$.

Example 15

Chiral Stationary Phase FSC 18

A mixture of isomers from Example 14 (0.70 g, 1.0 mmol) and silica gel LiChrospher Si 100 (2.0 g, 10 mm) are heated under reflux of dry toluene for 20 h. The modified silica is collected on G-4 filter, is washed with toluene, then with 2-propanol, and n-hexane. On drying at 70° C. for 4 h 1.94 g of FSC 18 are obtained.

Elem. anal. found: C, 5.78%; H, 1.14%; and N, 1.92%; indicates that 1.0 g of CSP contains 0.109 mmol of the bound selector.

Example 16

Stationary Phase FS

A mixture of Nucleosil 100-5 NH$_2$ (2.0 g, 3.49%C, 1.18% N, 1.94 mmol) and 2,4,5,6-tetrachloro-1,3-dicyanobenzene (1.0 g, 3.9 mmol) are heated in dry DMF (15.0 ml) at 100° C. for 20 h. The product is collected on filter, washed with DMF, then with dichloromethane and with MeOH. On drying at 70° C. for 4 h 1.2 g of stationary phase are obtained which has: Elem. anal. found : C, 5.57%; H, 1.07%; and N, 1.18%; indicates that 1.0 g of CSP contains 0.216 mmol of the bound material (based on C).

2.17 g of said stationary phase is heated in 1,2-diaminoethane (10.0 ml) for 16 h at 90° C. bath temperature. Product is collected on G4 filter, is washed with 1 m sodium carbonate, then methanol. On drying for 4 h at 70° C. is obtained 2.12 g of stationary phase FS.

Elem. anal. found: C, 6.19%; H, 1.33%; and N 1.24%; indicates that 1.0 g of CSP contains 0.021 mmol of the bound 1,2-diaminomethane (based on C).

Example 17

Chiral Stationary Phase FSC 19

To the suspension of FS of example 16 (2.0 g) in dry THF (20.0 ml) are added N-3,5-dinitrobenzoyl-L-leucine (1.9 g, 5.8 mmol) and EEDQ (1.44 g, 5.8 mmol). The reaction mixture is stirred for 16 h at ambient temperature, then FSC 19 is isolated as previously described, affording 2.24 g of the product.

Elem. anal. found : C, 12.98%; H, 1.41%; and N, 1.71%; indicates that 1.0 g of CSP contains 0.434 mmol of the bound DNB-Leu (based on C).

Example 18

Chiral Stationary Phase FSC 20

To the suspension of FS (2.0 g) in dry THF (20.0 ml) are added N-3,5-dinitrobenzoyl-L-phenylglycine (2.0 g, 5.82 mmol) and EEDQ (1.44 g, 5.8 mmol). The reaction mixture is stirred for 16 h at ambient temperature, then FSC 20 isolated as previously described, affording 2.23 g of the product.

Elem. anal. found: C, 12.58%; H, 1.77%; and N 2.09%; indicates that 1.0 g of CSP contains 0.354 mmol of the bound DNB-Phegly (based on C).

Example 19

4-[(2-amino)cyclohexylamino]-2,5,6-trichloro-1,3-dicyanobenzene

To the slurry of 2,4,5,6-tetrachloro-1,3-dicyanobenzene (2.0 g, 7.5 mmol) in acetonitrile (40 ml) triethylamine (5.0 ml) is added, then 1,2-diaminocyclohexane (0.86 g, 7.5 mmol) and the reaction mixture is heated under reflux for 1 h. It is cooled to ambient temperature, then deposited on ice for few hours, and the crystalline product is collected on filter. 2.32 g (89%) of the title product as pale-yellow powder are obtained.

IR (KBr): 3340, 3300, 3120, 2960, 2920, 2860, 2220, 1600, 1580, 1480, 1450, 1400, 1360, 1350, 1270, 1240, 1220, 1190, 1100, 1070, 1040, 990, 930, 900, 870, 850, 840, 740, 730 i 610 cm$^{-1}$.

Anal. calcd. for: $C_{14}H_{13}N_4Cl_3$ (343.63 g/mol): C, 48.93; H, 3.81; and N, 16.30. Found: C, 48.77; H, 4.01; and N, 16.35%.

Example 20

4-[2-(3,5-dinitrobenzoyl)amide-cyclohexyl]amino-2,5,6-trichloro-1,3-dicyanobenzene To the solution of the compound obtained in Example 19 in THF (40 ml) triethylamine (1.0 ml) is added, then solution of 3,5-dinitrobenzoylchloride (0.68 g, 295 mmol) in THF (10 ml). After 1 h stirring at ambient temperature the solvent is evaporated in vacuo and the solid residue is slurried in methanol (50 ml). After 10 min sonification in an ultrasound bath the product is collected on filter, is washed with methanol and dried to afford 1.18 g (75%) of white powder.

IR (KBr): 3300, 3260, 3100, 2920, 2860, 2220, 1640, 1570, 1540, 1510, 1340, 1200, 1100, 1080, 920, 870, 850, 770, 750 i 720 cm$^{-1}$.

Anal. calcd. for: $C_{21}H_{15}N_6O_5Cl_3$ (537.73 g/mol): C, 46.90; H, 2.81; and N, 15.63. Found: C, 46.97; H, 3.01; and N, 15.52%.

Example 21

4-{[2-(3,5-dinitrobenzoyl)-cyclohexyl]amide}-2,5-dichloro-6-(3-triethoxysilylpropyl)amino-1,3-dicyanobenzene, and 4-{[2-(3,5-dinitrobenzoyl)-cyclohexyl]amide)amino-5,6-dichloro-2-(3-triethoxysilylpropyl)amino-1,3-dicyanobenzene The compound from example 20 (1.0 g, 1.85. mmol) is dissolved in 3-aminopropyltriethoxysilane (5.0 ml) and DMF (1.0 ml) is added. Then the resulting solution is heated for 1 h at 100° C. bath temperature. After evaporation in vacuo, the crude product is purified on silica gel column (30 g), by elution with toluene. It is obtained a re 1:1 mixture of the title isomers (1.27 g, 94%).

IR (KBr): 3420, 3100, 2980, 2920, 2880, 2210, 2200, 1600, 1590, 1500, 1500, 1450, 1390, 1340, 1220, 1190, 1160, 1100, 1080, 950, 780, 730, 720, 680 cm$^{-1}$.

Anal. calcd. for $C_{30}H_{38}N_7O_8Cl_2Si$ (723.64): C, 49.78; H, 5.29; and N, 13.55. Found: C, 50.03; H, 5.75; and N, 13.28%.

Example 22 al Stationary Phase FSC 22

A mixture of isomers from example 21 (1.0 g, 1.35 mmol) and Nucleosil 100-5 (1.63 g) are heated for 20 h under reflux in dry toluene (15 ml). The product is collected on G-4 filter, washed first with toluene then with 2-propanol, and n-hexane. On drying at 70° C. for 4 h, 1.95 g of chiral stationary phase FSC 22 are obtained.

Elem. anal. found: C, 7.98%; H, 1.34%; and N, 1.26%; indicates that 1.0 g of FSC contains 0.128 mmol of the bound selector (based on C).

Example 23

Chiral Stationary Phase FSC 24

A suspension of FS prepared above (2.0 g), N-3,5-dinitrobenzoyl-L-phenylalanine (2.1 g; 5.8 mmol) and EEDQ (1.44 g; 5.8 mmol) in dry THF (20 ml) are stirred for 16 h at ambient temperature. The modified silica gel is collected on G-4 filter, washed with methanol and dried at 70° C. for 4 h to afford 2 g of FSC 24.

Example 24

Chiral Stationary Phase FSC 25

Silicagel LiChrospher 100 $NH_2$ (2.0 g) is slurried in THF (10 ml), then 2,4,5,6-tetrachloro-1,3-dicyanobenzene (0.67 g, 2.5 mmol) and EEDQ (0.60 g, 2.5 mmol) are added. The reaction mixture is stirred for 16 h at ambient temperature. Then N-3,5-dinitrobenzoylamido-D-phenylglycine(2-aminoethyl-(aminoethyl)-amide) (8.0 mmol) is added and stirring at 65° C. is continued for 6 h. The resulting stationary phase FSC 25 is collected on filter, washed with methanol, and dried at 70° C. for 4h. It is obtained ca 3 g of FSC 25.

Example 25

Chiral Stationary Phase FSC 26

Starting from silicagel Lichrospher 100 $NH_2$ (3.0 g) and 2,4,5,6-tetrachloro-1,3-dicyanobenzene (1.12 g, 4.2 mmol), and EEDQ (1.61 g, 6.5 mmol). The reaction mixture is stirred for 16 h at ambient temperature. Then N-3,5-dinitrobenzoylamido-D-phenylglycine-(meta-aminomethylphenyl)-methylamide (15.0 mmol) is added and stirring at 60° C. continued for 12 h. The resulting stationary phase is collected on filter, is washed with methanol, and dried at 70° C. for 4 h. It is obtained 4.4 g of the stationary phase FSC 26.

Example 26

Chiral Stationary Phase FSC 27

Silicagel Lichrospher 100 $NH_2$ (3.0 g) and 2,4,5,6-tetrachloro-1,3-dicyanobenzene (1.06 g, 4.0 mmol), are slurried in tetrahydrofurane (20 ml), and EEDQ (1.48 g, 6.0 mmol) is added. The reaction mixture is stirred for 16 h at ambient temperature. Then N-3,5-dinitrobenzoylamido-D-phenylglycine-(para-aminomethylphenyl)methyl-amide (12.0 mmol) is added and stirring at 60° C. continued for 8 h. The resulting stationary phase is collected on filter, is washed with methanol, and dried at 70° C. for 4 h. 4.2 g of the stationary phase FS 27 are obtained.

Example 27

Chiral Stationary Phase FSC 28

Starting from silica gel Lichrospher 100 $NH_2$ (6.0 g) and 2,4,5,6-tetrachloro-1,3-dicyanobenzene (2.66 g, 10 mmol), and EEDQ (3.71 g, 15 mmol). The reaction mixture is stirred for 16 h at ambient temperature Then N-3, 5dinitrobenzoylamido-D-phenylglycine-(2-aminocyclohexyl)amide (35 mmol) is added and stirring at 60° C. continued for 10 h. The resulting stationary phase is collected on filter, is washed with methanol, and dried at 70° C. for 4 h. 7.1 g of the FSC 28. are obtained.

Chemical analysis of chiral selectors and chiral stationary phases prepared according to the present invention

Example 28

Chiral Stationary Phase FSC 2

Analysis, found; C, 8.32; H, 1.21; N, 1.69%. According to elemental analysis 0.17 mmol of the chiral selector is bound on 1.0 g of silica gel.

Example 29

4-[(3,5-Dimethylanilido)-L-phenylalaninyl]-6-(3-triethoxysilyl)propylamino-2,5-dicloro-1,3-dicyanobenzene, and 4-[(3,5-dimethylanilido)-L-phenylalaninyl]-2-(3-triethoxysilyl)propylamino-5,6-dicloro, 1,3-dicyanobenzene IR (KBr): 3320, 3020, 2980, 2920, 2880, 2200, 1690, 1670, 1610, 1570,1500, 1460, 1440, 1390,1360, 1340,1320, 1215, 1160, 1100,950, 840, 790,770,740, 700,680 $cm^{-1}$.

Anal. calcd. for $C_{34}H_{41}N_5O_4Cl_2Si$ (682.69 g/mol): C, 59.81; H, 6.05 and N, 10.26. Found: C, 59.75; H, 6.15; and N, 10.29%.

Example 30

4-[(Naphth-1-yl)amido)-L-phenylalaninyl]-2-(3-triethoxypropyl) amino-5,6-dichloro-1,3-dicyanobenzene and 4-[(Naphth-1-yl)amido) -L-phenylalaninyl]-6-(3-triethoxypropyl)amino-2,5-dichloro-1,3-dicyanobenzene IR (KBr): 3400, 3350, 3060, 3020, 2980, 2920, 2880, 2720, 2200, 2220, 1690, 1670, 1590, 1510, 1450, 1400, 1370, 1350, 1300, 1270, 1250, 1200, 1160, 1100, 1080, 950, 800, 770, 750, 700 $cm^{-1}$.

Analysis calcd. for: $C_{36}H_{39}N_5O_4Cl_2Si$ (704.70 g/mol): C, 61.35; H, 5.57 and N, 9.94. Found: C, 61.12; H, 5.75; and N, 9.98%.

Example 31

Chiral Stationary Phase FSC 3

Anal. found: C, 8.99%; H, 0.98%; N, 1.58%. The % N reveals that 1.0 g of the stationary phase contains 0.23 mmol of chiral selector.

Example 32

Chiral Stationary Phase FSC 4

Anal. found: C, 8.02%; H, 1.03%; N, 1.65%. The % N reveals that 1.0 g of the stationary phase contains 0.23 mmol of chiral selector.

Example 33

4-[R-1-(naphth-1-yl)ethyl]amino-2-(3-triethoxysilylpropyl)amino-5,6-dichloro-1,3-dicyanobenzene and 4-[R-1-(naphth-1-yl)ethyl] amino-6-(3-triethoxysilylpropyl)amino-2,5-dichloro-1,3-dicyanobenzene IR (KBr): 3390, 3370, 2980, 2920, 2880, 2200, 1580, 1510, 1500, 1440, 1390, 1360, 1300, 1270, 1220, 1190, 1160, 1100,1070, 950, 760, 700 $cm^{-1}$.

Anal. calcd. for $C_{29}H_{34}N_4SiO_3Cl_2$ (585.57 g/mol): C, 59.47; H, 5.85 ; and N, 9.57%. Found: C, 59.41; H, 5.98; and N, 9.55%.

Example 34

Chiral Stationary Phase FSC, 6

Anal. found: C, 6.51%; H, 1.33%; N, 1.23%. According to % of N it is calculated that 1.0 g of the stationary phase contains 0.22 mmol of chiral selector.

Example 35

4-{n-butyl-[R-1-(naphth-1-yl)ethyl] acetamido}amino-6-(3-triethoxysilylpropyl)amino-2, 5-dichloro-1,3-dicyanobenzene, and 4-{n-butyl-[R-1 -(naphth-1-yl)ethyl]acetamido}amino-2-(3-triethoxysilylpropyl)amino-5, 6-dichloro-1,3-dicyanobenzene IR (KBr): 3390, 3100, 2980, 2920, 2880, 2220, 1670, 1575, 1520, 1460, 1420, 1390, 1360, 1340, 1310, 1290, 1240, 1210, 1190, 1160, 1100, 1080, 950, 800, 780 $cm^1$.

Anal. calcd. for $C_{35}H_{45}N_5SiO_4Cl_2$ (698.73 g/mol): C, 60.15; H, 6.49; and N, 10.02. Found: C, 60.27; H, 6.57; and N, 9.81%.

Example 36

Chiral Stationary Phase FSC 7

Analysis, found; C, 7.16%; H, 1.16%; N, 1.78%. According to elemental analysis. 0.25 mmol of the chiral selector is bound on 1.0 g of silica gel.

Example 37

4-{n-butyl-[N-R-1-(cyclohexyl)ethyl-N-3,5-dinitrobenzyl]acetamido}amino-6-(3-triethoxysilylpropyl)amino-2,5-dichloro-1,3-dicyanobenzene and 4-{n-butyl-[N-R-1-(cyclohexyl)ethyl-N-3,5-dinitrobenzyl] acetamido}amino-2-(3-triethoxysilylpropyl)amino-5, 6-dichloro-1,3-dicyanobenzene Anal. calcd. for $C_{38}H_{53}N_7SiO_8Cl_2$ (834.85 g/mol): C, 54.66; H, 6.39; and N, 11.74. Found: C, 54.73; H, 6.28; and N, 11.69.

Example 38

Chiral Stationary Phase FSC 9

Anal. found: C, 6.69%; H, 1.56%; and N, 1.78%. According on % of nitrogen: 0.18 mmol of chiral selector is bound at 1g of chiral stationary phase.

Example 39

4-{methyl-[R-1-(naphth-1-yl)ethyl]
acetamido}amino-2-(3-triethoxysilylpropyl)amino-5,
6-dichloro-1,3-dicyanobenzene, and 4-{methyl-[R-
1-(naphth-1-yl)ethyl]acetamido}amino-6-(3-
Triethoxysilylpropyl)amino-2, 5-dichloro-1,3-
dicyanobenzene IR (KBr): 3380, 2980, 2920, 2880, 2200, 1670, 1580, 1510, 1450, 1390, 1360, 1300, 1220, 1160, 1100, 950, 780 $cm^{-1}$.

Anal. calcd. for $C_{32}H_{39}N_5SiO_4Cl_2$ (656.66): C, 58.52; H, 5.98; and N, 10.66. Found: C, 58.48; H, 6.12; and N, 10.77%.

Example 40

Chiral Stationary Phase FSC 11

Anal. found C, 6.60%; H, 0.95%; and N, 1.27%. On the basis of nitrogen: 1.0 g of chiral stationary phase contain 0.18 mmol of chiral selector.

Example 41

Chiral Stationary Phase FSC 12

Anal. found. C, 8.83%; H, 1.38%; and N, 1.71%. On the basis of % N it is calculated that 1.0 g of chiral stationary phase contain 0.17 mmol of chiral selector.

Example 42

4-[3,5-dimethylanilido)-L-alaninyl]-Z 5-dichloro-6-
(3-triethoxysilylpropyl)amino-1,3-dicyanobenzene,
and 4-[3,5-dimethylanilido)-L-alaninyl]-5,6-
dichloro-2-(3-triethoxysilylpropyl)amino-1,3-
dicyanobenzene IR (KBr): 3325, 2980, 2920, 2880, 2200, 1680, 1610, 1590, 1510, 1450, 1390, 1200, 1160, 1100, 1080, 950, 840, 780, 690 $cm^{-1}$.

Anal. calcd. for $C_{28}H_{37}N_5O_4Cl_2Si$ (606.61): C, 55.43; H, 6.14; and N, 11.54. Found: C, 55.25; H, 6.16; and N, 11.82%.

Example 43

Chiral Stationary Phase FSC 14

Anal. found C, 6.42%; H, 1.14%; N, 1.52%. On the basis of % N it is calculated that 1.0 g of stationary phase contains 0.22 mmol of chiral selector.

Example 44

4-(cyclohexylamido-L-alaninyl)-2,5-dichloro-6-(3-
triethoxysilylpropyl)amino-1,3-dicyanobenzene, and
4-(cyclohexylamido-L-alaninyl)-5,6-dichloro-2-(3-
triethoxysilylpropyl)amino-1,3-dicyanobenzene IR (KBr): 3330, 2980, 2920, 2210, 1660, 1580, 1500, 1450, 1390, 1360, 1350, 1310,1290, 1250, 1220, 1200, 1160,1100,1070, 950, 890, 770 $cm^{-1}$.

Anal. calcd. for $C_{26}H_{39}N_5O_4Cl_2Si$ (584.60): C, 53.41; H, 6.72; and N, 11.98. Found: C, 53.18; H, 6.59; and N, 11.79%.

Example 45

Chiral Stationary Phase FSC 15

Anal. found C, 7.00%; H, 1.37%; and N, 1.49%. On the basis of % N it is calculated that 1.0 g of chiral stationary phase contains 0.21 mmol of chiral selector.

Example 56

4-[(3,5-dimethylanilido)-prolinyl]-Z5-dichloro-6-(3-
triethoxysilylpropyl)amino-1,3-dicyanobenzene, and
4-[(3,5-dimethylanilido)-prolinyl]5,6-Dichloro-2-(3-
triethoxysilylpropyl)amino 1,3-dicyanobenzene IR (KBr): 3330, 2990, 2960, 2940, 2200, 1680, 1610, 1580, 1530, 1450, 1390, 1350, 1300, 1200, 1160, 1000, 950, 840,780, 690 $cm^{-1}$.

Elem. anal. calcd. for $C_{30}H_{39}N_5O_4Cl_2Si$ (632.64): C, 56.95; H, 6.21; and N, 11.07. Found: C, 57.12; H, 5.96; and N, 11.02%.

Example 47

Chiral Stationary Phase FSC 16

Anal. found : C, 8.01%; H, 1.91%; and N, 1.72%; indicates that 1.0 g of CSP contains 0.25 mmol of the bound selector.

Example 48

4-(prolinyl-cyclohexylamide)-2,5-dichloro-6-(3-
triethoxysilylpropyl)amino-1,3-dicyanobenzene, and
4-(prolinyl-cyclohexylamide)-5,6-dichloro-2-(3-
triethoxysilylpropyl)amino-1,3-dicyanobenzene IR (KBr): 3440, 2990, 2960, 2940, 2200, 1660, 1580, 1520, 1470, 1450, 1390, 1350, 1300, 1200, 1190, 1160, 1100, 1080, 950, 780 $cm^{-1}$.

Anal. calcd. for $C_{28}H_{41}N_5O_4Cl_2Si$ (610.64): C, 55.06; H, 6.76; and N, 11.47. Found: C, 55.18; H, 6.38; and N, 11.30%.

Example 49

Chiral Stationary Phase FSC 17

Elem. anal. found : C, 7.42%, H, 1.67% and N, 1.63%, indicates that 1.0 g of CSP contains 0.23 mmol of the bound selector.

Example 50

4-{2-[2-(6-methoxy-naphth-2-yl)-propionylamido]
cyclohexyl}amino-6-(3-triethoxysilylpropyl)amino-
2,5-dichloro-1,3-dicyanobenzene and 4-{2-[2-(6-
methoxy-naphth-2-yl)-propionylamido]
cyclohexyl}amino-2-(3-triethoxysilylpropyl)amino-
5,6-dichloro-1,3-dicyanobenzene IR (KBr): 3350, 2940, 2200, 1650, 1580, 1510, 1450, 1390, 1350, 1260, 1200, 1160, 1070, 950, 850 i 770 $cm^{-1}$.

Anal. calcd. for $C_{37}H_{48}N_5O_5Cl_2Si$ (741.78 g/mol): C, 59.90; H, 6.52; and N, 9.44. Found: C, 60.04; H, 6.48; and N, 9.37%.

Example 51

Chiral Stationary Phase FSC 23

Elem. anal. found: C, 7.98%; H, 1.34%; and N, 1.26%; indicates that 1.0 g of CSP contains 0.172 mmol of the bound chiral selector (based on N).

Examples of Resolution of Racemates with Chiral
Stationary Phases According to the Present
Invention

Example 52

Resolution of Racemate with FSC

Chromatographic column for HPLC is filled with FSC and several racemic mixtures were separated using n-hexane/2-propanol (9:1) as eluent. Two enantiomers for each of mixture tested were resolved as completely separated symmetric peaks with $Rt_1$ and $Rt_2$ given in table 1 ($Rt_1$ and $Rt_2$ mean the retention time for each peak, in minutes):

TABLE 1

|  |  | $Rt_1$ | $Rt_2$ |
|---|---|---|---|
| FSC 10 | TR19 | 9.53 | 13.52 |
| FSC 8 | TR22 | 5.50 | 8.00 |
| FSC 7 | TR17 | 11.1 | 20.1 |

Example 53

Chromatographic Separation of Racemates with FSC

A number of racemic mixtures are employed as analytes to evaluate the chromatographic performance of several FSC. The eluent used is either n-hexane/2-propanol (9:1) (A) or n-hexane/dichloromethane/methanol (100:30:1) (B). The results are reported in Table 2.

What is claimed is:

1. A chiral selector of formula (I)

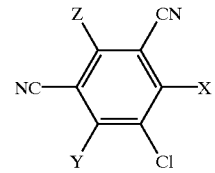

wherein:

$X = NR_1—CHR_2R_3$ $R_1$ is selected from: H, branched or linear alkyl having 1 to 6 carbon atoms, $R_2$ is selected from: the group consisting of H, branched or linear alkyl having 1 to 6 carbon atoms, aryl or arylalkyl, containing or not containing a heteroatom, being said aryl or arylalkyl substituted or unsubstituted with —OH or —CH$_2$CONH$_2$,

TABLE 2

Separation of several racemic analytes listed in FIG. 6 with the stationary phases of the invention.
The letter in brackets refers to the eluent used.

racemic analyte

| | FSC 10 (A) | | | FSC 8 (A) | | | FSC 18 (A) | | | FSC 13 (A) | | |
|---|---|---|---|---|---|---|---|---|---|---|---|---|
| TR17 | $k'_1$ | $k'_2$ | $R_s$ | $k'_1$ | $k'_2$ | $R_s$ | $k'_1$ | $k'_2$ | $R_s$ | $k'_1$ | $k'_2$ | $R_s$ |
| | 6.10 | 8.59 | 2.62 | 3.96 | 5.17 | 2.45 | 2.64 | 8.75 | 13.41 | 3.81 | 3.93 | 0.21 |
| | FSC 11 (A) | | | FSC 7 (A) | | | FSC 10 (A) | | | FSC 18 (A) | | |
| TR19 | $k'_1$ | $k'_2$ | $R_s$ | $k'_1$ | $k'_2$ | $R_s$ | $k'_1$ | $k'_2$ | $R_s$ | $k'_1$ | $k'_2$ | $R_s$ |
| | 5.19 | 10.89 | 7.29 | 3.91 | 7.74 | 5.28 | 3.96 | 6.04 | 3.98 | 1.29 | 6.60 | 17.97 |
| | FSC 3 (B) | | | FSC 7 (A) | | | FSC 8 (A) | | | FSC 18 (A) | | |
| TR23 | $k'_1$ | $k'_2$ | $R_s$ | $k'_1$ | $k'_2$ | $R_s$ | $k'_1$ | $k'_2$ | $R_s$ | $k'_1$ | $k'_2$ | $R_s$ |
| | 2.61 | 3.57 | 3.37 | 8.43 | 17.8 | 6.31 | 5.09 | 7.26 | 6.25 | 3.06 | 10.26 | 3.77 |
| | FSC 1 (A) | | | FSC 5 (A) | | | FSC 13 (A) | | | FSC 20 (A) | | |
| TR6 | $k'_1$ | $k'_2$ | $R_s$ | $k'_1$ | $k'_2$ | $R_s$ | $k'_1$ | $k'_2$ | $R_s$ | $k'_1$ | $k'_2$ | $R_s$ |
| | 2.08 | 2.18 | 0.50 | 2.99 | 3.25 | 0.72 | 1.31 | 1.41 | 0.69 | 1.51 | 1.79 | 0.58 |
| | FSC 1 (B) | | | FSC 13 (B) | | | FSC 12 (B) | | | FSC 20 (A) | | |
| TR8 | $k'_1$ | $k'_2$ | $R_s$ | $k'_1$ | $k'_2$ | $R_s$ | $k'_1$ | $k'_2$ | $R_s$ | $k'_1$ | $k'_2$ | $R_s$ |
| | 2.03 | 2.16 | 0.84 | 4.84 | 5.08 | 0.78 | 3.54 | 3.82 | 1.02 | 11.46 | 14.53 | 0.72 |
| | FSC 11 (B) | | | FSC 12 (A) | | | FSC 4 (A) | | | FSC 19 (A) | | |
| TR9 | $k'_1$ | $k'_2$ | $R_s$ | $k'_1$ | $k'_2$ | $R_s$ | $k'_1$ | $k'_2$ | $R_s$ | $k'_1$ | $k'_2$ | $R_s$ |
| | 2.52 | 2.65 | 0.55 | 1.62 | 1.76 | 0.58 | 1.06 | 1.22 | 0.34 | 2.89 | 3.53 | 0.37 |
| | FSC 11 (A) | | | FSC 7 (A) | | | FSC 3 (A) | | | FSC 12 (A) | | |
| TR15 | $k'_1$ | $k'_2$ | $R_s$ | $k'_1$ | $k'_2$ | $R_s$ | $k'_1$ | $k'_2$ | $R_s$ | $k'_1$ | $k'_2$ | $R_s$ |
| | 1.40 | 1.56 | 0.84 | 0.26 | 0.28 | 0.89 | 0.25 | 0.44 | 1.31 | 2.77 | 2.95 | 0.82 |

$R_3$ is selected from: branched or linear alkyl having 1 to 6 carbon atoms, $(CH_2)_p$—COOH, $(CH_2)_p$—CONH$_2$, $(CH_2)_p$—CONHR$_4$, $(CH_2)_p$—NHCOR$_4$, $(CH_2)_p$—CON($R_4R_5$), CONHCH($R_4$)CONHR$_4$, $(CH_2)_p$—NHCOCH($R_4$)NHCOR$_4$, $C_6H_4$—$CH_2$—NHCOCH($R_4$)NHCOR$_4$ and $CH_2NH(CH_2)_p$—NHCOCH($R_4$)NHCOR$_4$, where p is an integer from 0 to 4, $R_4$ and $R_5$ are independently selected from the group consisting of:
(a) linear or cyclic alkyl having from 1 to 6 carbon atoms,
(b) aryl, and
(c) a spacer group of formula —$(CH_2)_n$—Si—$(OR_6)_3$ where n ranges from 1 and 10 and $R_6$ is an alkyl with 1 to 4 carbon atoms;
said groups (a) and (b) being substituted or unsubstituted with alkyl with 1 to 4 carbon atoms, aryl, cycloalkyl having 5–6 carbon atoms, $NO_2$ and $OCH_3$, or:
(i) $R_1$ forms together with $R_2$, with the carbon atom bound to $R_2$ and with the nitrogen, a 5–6 membered ring, or
(ii) $R_2$ forms with $R_3$ and with the carbon atom bound to $R_2$ and $R_3$ a 5–6 membered ring substituted by —NHCOR$_4$, or by —NHCOCH($R_4$)NHCOR$_4$, where $R_4$ is selected from the group consisting of:
(a) linear or cyclic alkyl having from 1 to 6 carbon atoms,
(b) aryl, and
(c) a spacer group of formula —$(CH_2)_n$—Si—$(OR)_3$ where n ranges from 1 and 10 and $R_6$ is an alkyl with 1 to 4 carbon atoms,
said groups (a) and (b) being unsubstituted or substituted from the group consisting of 1 to 4 carbon atom alkyl, aryl, cycloalkyl having 5–6 carbon atoms, $NO_2$ and $OCH_3$,
Y and Z independently of each other are selected from the group consisting of chloro, X group where X is defined above, a spacer group of formula —$A(CH_2)_n$—Si—$(OR_6)_3$ where A represents NH or O, and n and $R_6$ are defined above;
with the proviso that said formula (I) contains: (a) one to three X groups containing at least one chiral atom, and (b) only one spacer group as above defined.

2. The chiral selector according to claim 1, wherein:
$R_1$ is selected from H, branched or linear alkyl having 1 to 6 carbon atoms;
$R_2$ is selected from H, branched or linear alkyl having 1 to 6 carbon atoms, aryl, arylalkyl, $CH_2CONH_2$, or $R_1$ forms with $R_2$, with the carbon atom bound to $R_2$ and with N a 5–6 membered ring; and
$R_3$ is selected from a branched or linear alkyl having 1 to 6 carbon atoms, $(CH_2)_p$—CONHR$_4$, $(CH_2)_p$—CON($R_4R_5$), where p, $R_4$ and $R_5$ have the meanings given above.

3. The chiral selector according to claim 1, wherein:
$R_1$ is H, $R_2$ is H, $R_3$ is selected from $(CH_2)_p$—NHCOR$_4$, $CH_2$—NHCOR$_4$, where p, $R_4$ have the meanings given above; or $R_2$ forms with $R_3$ and the carbon atom bound to $R_2$ and $R_3$ a 5–6 membered ring.

4. The chiral selector according to claim 1, wherein:
$R_1$ is H, $R_2$ is H, or $R_2$ forms with $R_1$, with the carbon atom bound to $R_2$ and with N a 5–6 membered ring; $R_3$ is CONHCH($R_4$)CONHR$_4$, where p, $R_4$ have the meanings given above.

5. The chiral selector according to claim 1, wherein:
$R_1$ is H, $R_2$ is H, $R_3$ is selected from: $(CH_2)_p$—NHCOCH($R_4$)NHCOR$_4$, $C_6H_4$—$CH_2$—NHCOCH($R_4$)NHCOR$_4$, $CH_2NH(CH_2)_p$—NHCOCH($R_4$)NHCOR$_4$; or R2 forms with R3 and with the carbon atom bound to R2 and R3 a 5–6 membered ring substituted with NHCOCH($R_4$)NHCOR$_4$; p and $R_4$ having the meanings given above.

6. A chiral stationary phase compound of formula (I)

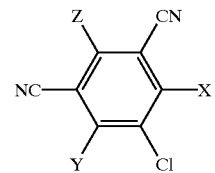

wherein:
X=NR$_1$—CHR$_2$R$_3$
$R_1$ is selected from: H, branched or linear alkyl having 1 to 6 carbon atoms,
$R_2$ is selected from: H, branched or linear alkyl having 1 to 6 carbon atoms, aryl or arylalkyl, containing or not containing, a heteroatom, being said aryl or arylalkyl substituted or unsubstituted with —OH, or —$CH_2CONH_2$,
$R_3$ is selected from: branched or linear alkyl having 1 to 6 carbon atoms, $(CH_2)_p$—COOH, $(CH_2)_p$—CONH$_2$, $(CH_2)_p$—CONHR$_4$, $(CH_2)_p$—NHCOR$_4$, $(CH_2)_p$—CON($R_4R_5$), CONHCH($R_4$) CONHR$_4$, $(CH_2)_p$—NHCOCH($R_4$)NHCOR$_4$, $C_6H_4$—$CH_2$—NHCOCH($R_4$)NHCOR$_4$, $CH_2NH(CH_2)_p$— NHCOCH($R_4$)NHCOR$_4$, where p is an integer from 0 to 4, $R_4$ and $R_5$ are independently selected from the group consisting of:
(a) linear or cyclic alkyl having from 1 to 6 carbon atoms,
(b) aryl, and
(c) a spacer group of formula —$(CH_2)_n$—Si—$(OR_6)_3$ where n ranges from 1 and 10 and $R_6$ is an alkyl having 1 to 4 carbon atoms;
said groups (a) and (b) being unsubstituted or substituted from the group consisting of 1 to 4 carbon atom alkyl, aryl, cycloalkyl having 5–6 carbon atoms, $NO_2$ and $OCH_3$, or:
(i) $R_1$ forms together with $R_2$, with the carbon atom bound to $R_2$ and with the nitrogen, a 5–6 membered ring, or
(ii) $R_2$ forms with $R_3$ and with the carbon atom bound to $R_2$ and $R_3$ a 5–6 membered ring substituted by —NHCOR$_4$, or by —NHCOCH($R_4$)NHCOR$_4$, where $R_4$ is selected from the group consisting of:
(a) a linear or cyclic alkyl having 1 to 6 carbon atoms,
(b) aryl,
(c) a spacer group of formula —$(CH_2)_n$—Si—$(OR_6)_3$ where n is comprised between 1 and 10 and $R_6$ is an alkyl having 1 to 4 carbon atoms;
said groups (a) and (b) being unsubstituted or substituted with alkyl having 1 to 4 carbon atoms, aryl, cycloalkyl having 5–6 carbon atoms, $NO_2$ and $OCH_3$,
Y and Z independently of each other are selected from the group consisting of: chloro, X group where X has the meanings given above, a spacer group of formula —A(CH$_2$)$_n$—Si—(OR$_6$)$_3$ where A represents NH or O, and n and R$_6$ have the meanings given above;

with the proviso that said formula (I) contains: (a) one to three X groups containing at least one chiral atom, and (b) only one spacer group as above defined, said compound of formula (I) being bound to a solid organic or inorganic support by means of said spacer group.

7. The compound according to claim 6, wherein the solid support is selected from the group consisting of silica, silica gel, alumina, kaolin, titanium oxide, magnesium, silicate and synthetic polymers.

8. A process for the preparation of chiral stationary phases of claim 6, further comprising the following separate reaction steps which can take place in any order:

(a) introducing one or more chiral groups X on the 1,3-dicyanobenzene ring, said X group having the structure defined in claim 6, (b) introducing the spacer group either on 1,3-dicyanobenzene ring, or on a X chiral group already present on the 1,3-dicyanobenzene ring, said spacer group having the structure defined in claim 6, and (c) forming a covalent linkage between the spacer group and a solid support.

9. The process according to claim 8, wherein the X groups are introduced on the 1,3-dicyanobenzene ring by using reagents containing the X group selected from the group consisting of esters of amino acids, amides of amino acids, arylalkylalchols, arylcarboxylic acids, arylcarboxylic acid esters, arylcarboxylic acid esters, aminoamides and arylalkylamines.

10. The process according to claim 9, wherein said reagents containing the X group are selected from the group consisting of 1-phenylethylamine, proline, (1-(naphth-1-yl) ethylamine, phenylalanine, phenylglycine, n-butylamine, naphthylethylamine, 3,5-dimethylaniline, cyclohexylethylamine, sarcosine and asparagine.

11. The process of analytical or preparative chromatographic separation of enantiomers or mixtures of racemates, comprising the steps of preparing chiral stationary phases according to claim 6.

12. The process according to claim 11, wherein the separation is carried out by high performance liquid chromatography (HPLC).

* * * * *